United States Patent [19]

Kamiya et al.

[11] Patent Number: 5,128,465
[45] Date of Patent: Jul. 7, 1992

[54] PROCESS FOR THE PREPARATION OF CEPHEM DERIVATIVES AND INTERMEDIATES THEREFOR

[75] Inventors: Takashi Kamiya; Toshihiko Naito; Yuuki Komatu; Yasunobu Kai, all of Ibaraki; Takaharu Nakamura, Chiba; Manabu Sasho, Ibaraki; Shigeto Negi, Ibaraki; Isao Sugiyama, Ibaraki; Kanemasa Katsu, Ibaraki; Hiroshi Yamauchi, Ibaraki, all of Japan

[73] Assignee: Eisai Co., Ltd., Tokyo, Japan

[21] Appl. No.: 468,319

[22] Filed: Jan. 22, 1990

Related U.S. Application Data

[62] Division of Ser. No. 323,781, Mar. 15, 1989, abandoned.

[30] Foreign Application Priority Data

Mar. 16, 1988 [JP] Japan .................................. 63-60511

[51] Int. Cl.$^5$ .............................................. C07D 501/24
[52] U.S. Cl. ..................................... 540/222; 540/225
[58] Field of Search ............... 540/225, 217, 222, 215

[56] References Cited

U.S. PATENT DOCUMENTS

| | | | |
|---|---|---|---|
| 4,486,586 | 12/1984 | Narita et al. | 540/222 |
| 4,632,918 | 12/1986 | Angerbauer et al. | 540/222 |
| 4,751,295 | 6/1988 | Oka et al. | 540/222 |
| 4,921,850 | 5/1990 | Kamiya et al. | 540/225 |

*Primary Examiner*—Robert T. Bond
*Assistant Examiner*—E. C. Ward
*Attorney, Agent, or Firm*—Wenderoth, Lind & Ponack

[57] ABSTRACT

A cephem derivative represented by the following formula:

wherein $R_1$ means a fluorine-substituted lower alkyl and $A_1$ denotes a cyclic or acyclic ammonio group, or a non-toxic salt thereof, is prepared by reacting a compound represented by the following formula:

wherein $A_1$ has the same meaning as defined above, with another compound represented by the following formula:

wherein $R_1$ has the same meaning as defined above, and if necessary, removing the protecting groups.

3 Claims, No Drawings

PROCESS FOR THE PREPARATION OF CEPHEM DERIVATIVES AND INTERMEDIATES THEREFOR

This is a divisional of Ser. No. 07/323,781 filed Mar. 15, 1989, now abandoned.

BACKGROUND OF THE INVENTION

1) Field of the Invention

This invention relates to a process for the preparation of novel cephem derivatives useful as antibiotic agents and also to synthesis intermediates therefor.

2) Description of the Related Art

Cephem derivatives having an ammoniopropenyl group at the 3-position thereof have heretofore been disclosed in Japanese Patent Application Laid-Open Nos. 172493/1984 (U.S. Pat. No. 4,486,586) and 5084/1986 (U.S. Pat. No. 4,751,295).

SUMMARY OF THE INVENTION

The present inventors have found that novel cephem derivatives having an ammoniopropenyl group at the 3-position thereof and a fluorine-substituted lower alkoxyimino group at the 7-side chain thereof have excellent antibacterial activities, leading to establishment of their preparation process.

An object of this invention is therefore to provide a process for the preparation of such cephem derivatives and also synthesis intermediates therefor.

In one aspect of this invention, there is thus provided a process for the preparation of a cephem derivative represented by the following formula:

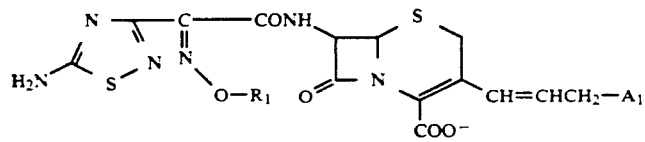

(I)

wherein $R_1$ means a fluorine-substituted lower alkyl and $A_1$ denotes a cyclic or acyclic ammonio group, or a non-toxic salt thereof, which comprises reacting a compound represented by the following formula:

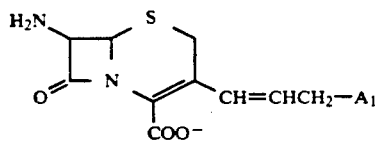

(II)

wherein $A_1$ has the same meaning as defined above, a compound obtained by blocking the $-COO^-$ of said another compound with a protecting group, or a salt thereof, with another compound represented by the following formula:

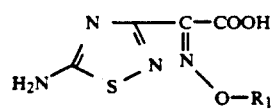

(III)

wherein $R_1$ has the same meaning as defined above, a compound obtained by blocking the amino group of the first-mentioned compound with a protecting group, a reactive derivative of the first-mentioned compound at the carboxyl group thereof, or a salt thereof and if necessary, removing the protecting groups.

In another aspect of this invention, there is also provided a compound represented by the following formula:

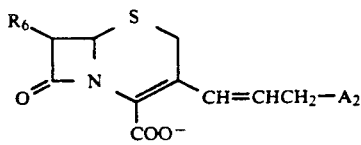

wherein $R_6$ means an amino group or an amino group blocked by a protecting group, and $A_2$ denotes a group represented by the following formula:

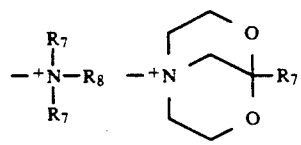

all $R_7$ being either the same or different and meaning individually a lower alkyl group and $R_8$ denoting a lower alkyl group substituted by a hydroxyl group and/or a carbamoyl group, a compound obtained by blocking $-COO^-$ of the first-mentioned compound with a protecting group, or a salt thereof.

In a further aspect of this invention, there is also provided a process for the preparation of the compound, $-COO^-$-protected derivative thereof or salt according to said another aspect of this invention. The process comprises reacting a compound represented by the following formula:

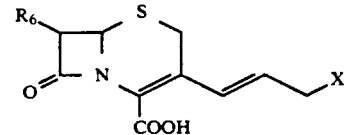

wherein $R_6$ has the same meaning as defined above and X denotes a halogen atom, a compound obtained by blocking the carboxyl group of the last-mentioned compound with a protecting group or a salt thereof with an amine corresponding to $A_2$ or a salt thereof; and if necessary, removing the protecting group.

The compounds according to the first aspect of this invention have strong antibacterial activities against gram-negative bacteria and gram-positive bacteria and are useful as antibacterial agents.

DETAILED DESCRIPTION OF THE INVENTION AND PREFERRED EMBODIMENTS

As illustrative examples of the fluorine-substituted alkyl group represented by $R_1$ in the formula (I), may be mentioned fluoromethyl, difluoromethyl, 2-fluoroethyl, 2,2-difluoroethyl, 2,2,2-trifluoroethyl, 1-fluoroethyl, 2-fluoropropyl, 1-(fluoromethyl)-2-fluoroethyl, 3-fluoropropyl, etc. Of these, fluoromethyl is particularly preferred.

Illustrative examples of the acyclic ammonio group represented by $A_1$ in the formula (I) may include the following groups:

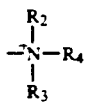

wherein $R_2$, $R_3$ and $R_4$ may be the same or different and mean individually a group selected from lower alkyl, hydroxyl-substituted lower alkyl, carbamoyl-substituted lower alkyl, cyano-substituted lower alkyl, amino, (lower alkyl)carbonylamino-substituted lower alkyl, aminosulfonyl-aminocarbonyl-substituted lower alkyl, (lower alkyl)-sulfonylaminocarbonyl-substituted lower alkyl, (lower alkyl)aminocarbonyl-substituted lower alkyl, hydroxyl- and carbamoyl-substituted lower alkyl, hydroxyl- and hydroxy(lower alkyl)aminocarbonyl-substituted lower alkyl, (lower alkyloxy)aminocarbonyl-substituted lower alkyl, hydroxyaminocarbonyl-substituted lower alkyl, carbamoyl(lower alkyl)aminocarbonyl-substituted lower alkyl, hydroxy(lower alkyl)aminocarbonyl-substituted lower alkyl, (lower alkyl)amino-substituted lower alkyl, [carboxylate(lower alkyl)di(lower alkyl)ammonio]-substituted lower alkyl, di(lower alkyl)amino-substituted lower alkyl, di(lower alkyl)amino- and hydroxyl-substituted lower alkyl, ureido, hydroxyl, carboxyl-substituted lower alkyl, hydroxy- and carbamoyl-substituted lower alkyl, (lower alkyloxy)-substituted lower alkyl, di(lower alkyl)aminocarbonyl-substituted lower alkyl, dicarbamoyl-substituted lower alkyl, bis[hydroxy(lower alkyl)]aminocarbonyl-substituted lower alkyl, dihydroxy-substituted lower alkyl, trihydroxy-substituted lower alkyl, bis[hydroxy(lower alkyl)]amino-substituted lower alkyl, amino-substituted lower alkyl, oxo-substituted lower alkyl, di(lower alkyl)amino-substituted lower alkyl, and 5-membered-heterocyclic-ring-substituted lower alkyl (as the 5-membered heterocyclic ring group, pyrazolyl, imidazolyl, oxadiazolyl, tetrazolyl or the like may be mentioned by way of example) groups. On the other hand, the following groups may be mentioned as examples of the cyclic ammonio group represented by $A_1$ in the formula (I).

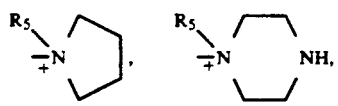

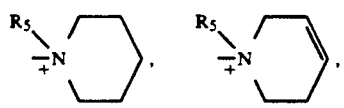

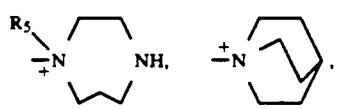

-continued

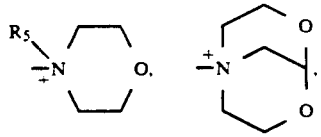

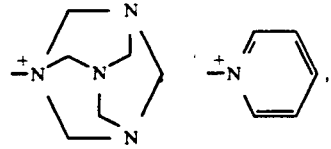

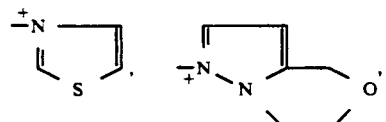

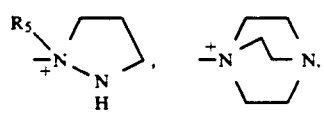

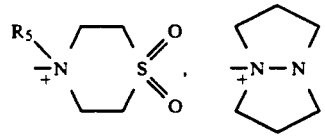

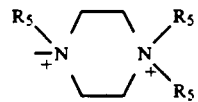

wherein $R_5$ means a group selected from lower alkyl, carbamoyl-substituted lower alkyl, amino-substituted lower alkyl, hydroxyl-substituted lower alkyl, carboxyl-substituted lower alkyl, cyano-substituted lower alkyl, dihydroxy-substituted lower alkyl and ureido-substituted lower alkyl groups, and the cyclic ammonio group may contain on its ring one or more hydroxy-substituted lower alkyl, hydroxyl, formyl, sulfonic, carboxyl-substituted lower alkyl, carbamoyl, sulfamoyl, carboxyl, hydroxyimino-substituted lower alkyl, imino-substituted lower alkyl, bis[hydroxy(lower alkyl)]aminocarbonyl, hydroxy(lower alkyl)aminocarbonyl, amino, morpholinocarbonyl, carboxy(lower alkyloxy)-substituted lower alkyl, carboxy(lower alkyl)thio, lower alkyl and sulfo-substituted lower alkyl groups.

Illustrative examples of the lower alkyl groups in the definition of $A_1$ ($R_2$-$R_5$) in the formula (I) may include alkyl groups having 1-4 carbon atoms such as methyl, ethyl, n-propyl, i propyl, n-butyl, i-butyl, sec-butyl and t-butyl.

As non-toxic salts of the compounds of the formula (I), may be mentioned their pharmaceutically-acceptable salts, for example, alkali metal salts such as sodium salts and potassium salts; ammonium salts; quaternary ammonium such as tetraethylammonium salts and betaine salts; alkaline earth metal salts such as calcium salts and magnesium salts; inorganic acid salts such as hydrochlorides, hydrobromides, hydroiodides, sulfates, carbonates and bicarbonates; organic carboxylates such as acetates, maleates, lactates and tartrates; organic sulfonates such as methanesulfonates, hydroxymethanesulfonates, hydroxyethanesulfonates, taurine salts, benzenesulfonates and toluenesulfonates; amino acid salts such as arginine salts, lysine salts, serine salts, aspartates, glutamates and glycine salts; amine salts such as trimethylamine salts, triethylamine salts, pyridine salts, procaine salts, picoline salts, dicyclohexylamine salts, N,N'-dibenzylethylenediamine salts, N-methylglucamine salts, diethanolamine salts, triethanolamine salts, tris(hydroxymethylamino)methane salts and phenethylbenzylamine salts; etc.

Each of the compounds of the formula (I) has its syn-isomer (Z) and anti-isomer (E) with respect to its stereoscopic configuration at the following moiety:

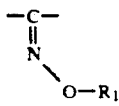

Although both isomers are included in the present invention, the syn-isomers are desired from the standpoint of antibacterial activities.

As the salts of the compounds of the general formulae (II) and (III) and the protecting groups for the compounds, those employed routinely may also be used so long as they do not impair the above reaction.

Exemplary protecting groups for the amino group may include formyl group, acetyl group, chloroacetyl group, dichloroacetyl group, phenylacetyl group, thienylacetyl group, t-butoxycarbonyl group, benzyloxycarbonyl group, trityl group, p-methoxybenzyl group, diphenylmethyl group, benzylidene group, p-nitrobenzylidene group, m-nitrobenzylidene group 3,4-methylenedioxybenzylidene group, m-chlorobenzylidene group. As illustrative protecting groups for the —COO⁻ group, may be mentioned usual protecting groups for a carboxyl group, namely, p-methoxybenzyl group, p-nitrobenzyl group, t-butyl group, methyl group, 2,2,2-trichloroethyl group, diphenylmethyl group and pivaloyloxymethyl group, etc. Here, use of a silylating agent such as N,O-bis(trimethylsilyl)acetamide, N-methyl-N-(trimethylsilyl)acetamide, N-methyl-N-(trimethylsilyl)trifluoroacetamide or N-(trimethylsilyl)acetamide is convenient because such a silylating agent can protect both the amino group and the carboxyl group at the same time.

As salts of the compounds of the formulae (II) and (III), suitable selection may be made from their salts, for example, alkali metal salts such as sodium salts and potassium salts; alkaline earth metal salts such as calcium salts and magnesium salts; ammonium salts; quaternary ammonium salts such as triethylammonium salts and betaine salts; inorganic acid salts such as hydrochlorides, hydrobromides, sulfates, carbonates, hydroiodides and bicarbonates; organic carboxylates such as acetates, trifluoroacetates, maleates, lactates and tartrates; organic sulfonates such as methanesulfonates, hydroxymethanesulfonates, hydroxyethanesulfonates, taurine salts, benzenesulfonates and toluenesulfonates; amine salts such as trimethylamine salts, triethylamine salts, pyridine salts, procaine salts, picoline salts, dicyclohexylamine salts, N,N'-dibenzylethylenediamine salts, N-methylglucamine salts, diethanolamine salts, triethanolamine salts, tris(hydroxymethylamino)methane salts and phenethylbenzylamine salts; amino acid salts such as arginine salts, aspartates, lysine salts, glutamates, serine salts and glycine salts; etc.

Where —COO⁻ is blocked by any protecting group in the compound of the formula (II), an ammonium salt is formed between anions such as iodine ions, chlorine ions or bromine ions and ammonio groups represented by $A_1$.

The preparation process of this invention can be carried out under conventional reaction conditions for N-acylation. For example, the reaction can be conducted in an inert solvent, in the presence or absence of a base, at −50° C. to 50° C. preferably −20° C. to 30° C. As exemplary inert solvents, may be mentioned acetone, tetrahydrofuran, N,N-dimethylformamide, N,N-dimethylacetamide, dioxane, dichloromethane, chloroform, benzene, toluene, acetonitrile, and mixed solvents thereof. Illustrative examples of the base may embrace N,N-dimethylaniline, triethylamine, pyridine, N-methylmorpholine, etc.

When a carboxylic acid (—COOH) represented by the formula (III) is used in the process of this invention, it is preferable to conduct the reaction in the presence of a condensation agent such as, for example, N,N'-dicyclohexylcarbodiimide, N,N'-diethylcarbodiimide, N-cyclohexyl-N'-morpholinoethylcarbodiimide, a trialkyl phosphite, poly(ethyl phosphate) or p-toluenesulfonic acid chloride. When a reactive derivative at the carboxyl group of the formula (III) is employed, it is possible to use as the reactive derivative an acid halide such as an acid chloride or acid bromide; a symmetric acid anhydride; a mixed acid anhydride with a carboxylic acid such as ethyl chlorocarbonate, trimethylacetic acid, thioacetic acid or diphenylacetic acid; an active ester with 2-mercaptopyridine, cyanomethanol, p-nitrophenol, 2,4-dinitrophenol or pentachlorophenol; an active thioester with 2-mercaptobenzothiazole or the like; an active acid amide with saccharine or the like; or the like.

Each protecting group can be removed by a method known per se in the art in accordance with the kind of the protecting group used, such as hydrolysis or reduction.

Compounds represented by the following formula:

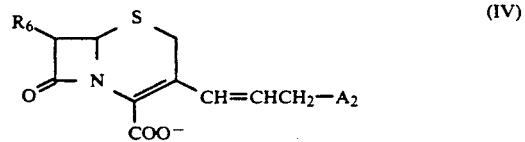

wherein $R_6$ means an amino group or an amino group blocked by a protecting group, and $A_2$ denotes a group represented by the following formula:

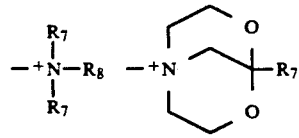

all $R_7$ being either the same or different and meaning individually a lower alkyl group and $R_8$ denoting a lower alkyl group substituted by a hydroxyl group and/or a carbamoyl group, compounds obtained by blocking —COO⁻ of the first-mentioned compounds with a protecting group, and salts thereof are synthesis intermediates for the compounds of the formula (I) and are novel compounds.

As specific examples of $R_8$ in $A_2$ which is in turn contained in the formula (IV), may be mentioned carbamoylmethyl group, carbamoylethyl group, 1-carbamoyl-2-hydroxyethyl group, 1-carbamoylethyl group, 2-hydroxypropyl group and the like. As the lower alkyl groups represented by $R_7$ and $R_8$ respectively, $C_1$–$C_4$ alkyl groups may be mentioned by way of example. As protecting groups for the $-COO^-$ and amino group, the same protecting groups as referred upon description of the compounds of formulae (II) and (III) may be mentioned. As exemplary salts, may be mentioned inorganic acid salts such as hydrochlorides, hydrobromides, hydroiodides, sulfates, carbonates and bicarbonates and perchlorate; organic carboxylates such as acetates, maleates, lactates, tartrates and trifluoroacetate; organic sulfonates such as methanesulfonates, benzenesulfonates, toluenesulfonates, hydroxymethanesulfonates, hydroxyethanesulfonates and taurine salts; amino acid salts such as aspartates and glutamates. Where $-COO^-$ is blocked by a protecting group in the compound of the formula (I), an ammonium salt is formed between anions such as iodine ions, chlorine ions or bromine ions and the ammonio groups represented by $A_2$.

Compounds of the formula (IV), compounds obtained by blocking $-COO^-$ of the compounds (IV) with a protecting group, and salts thereof can each be obtained by reacting a compound represented by the following formula:

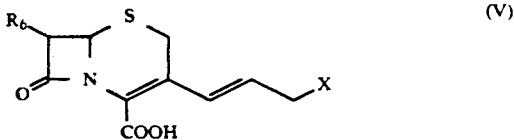

wherein $R_6$ has the meaning as defined above and X denotes a halogen atom, a compound obtained by blocking the carboxyl group of the compound (V) with a protecting group or a salt thereof with an amine corresponding to $A_2$ or a salt thereof; and if necessary, removing the protecting group.

The above reaction can be conducted, for example, in an inert solvent—such as acetone, tetrahydrofuran, N,N-dimethylformamide, methylene chloride, chloroform or acetonitrile—at a reaction temperature of from $-10°$ C. to $50°$ C.

As protecting groups for the carboxyl and amino groups, protecting groups similar to those described above with respect to the $-COO^-$ and amino group in the compounds of the formulae (II) and (III) can be used. The salt of the compound of the formula (V) and the salt of the amine corresponding to $A_2$ may be chosen suitably from those exemplified as salts of the compounds of the formulae (II) and (III). Illustrative examples of the halogen atom represented by X may include chlorine atom, iodine atom and bromine atom.

Among the amines corresponding to $A_1$ and $A_2$ respectively, the following compounds and their salts are novel compounds and as already described above, can be used as synthesis intermediates.

wherein $R_7$ has the same meaning as defined above.

As salts of these compounds, may be mentioned those exemplified as salts of the compounds of formula (IV).

The compounds of the formula (VI) and their salts can each by obtained by subjecting ethylmethylamine to cyanomethylation and then amidating the nitrile through hydrolysis.

The compounds of the formula (VII) and their salts can each by obtained by dimethylating serine amide. They can also be obtained by subjecting the methyl ester of N,N-dimethylserine to ammonolysis. As a further alternative, they can also be obtained by amidating N-benzyl-N-methylserine, converting the reaction product into a quaternary form with a methyl halide and then removing the benzyl group.

The compounds of the formula (VIII) and their salts can each be obtained by reacting diethanol amine with a halogenated methylcarbonyl(lower alkyl) such as bromoacetone.

As already mentioned above, the invention compounds of the formula (I) have strong antibacterial activities against both gram-positive and gram-negative bacteria and are hence useful as anti-bacterial agents.

When using the compounds of this invention as injections, they may be administered generally at a daily dose of 100 mg–10 g in 1–4 portions either intravenously or intramuscularly. Needless to say, the dose may be increased or decreased depending on the age and conditions of disease.

Their injections may be produced by a method known per se in the art. For example, each compound of this invention may be formulated into an injection by dissolving same in distilled water, if necessary, in the presence of an isotonic agent, solubilizer and/or the like. They may each be filled as powder in a vial or the like, thereby providing injections which require dissolution before use. These injections are hence dissolved in distilled water for injections, physiological saline, glucose injection, amino acid infusion or the like upon administration.

The present invention will next be described in further detail by the following Experiments and Examples.

EXPERIMENT 1

Ethyl 2-(5-Tritylamino-1,2,4-Thiadiazol-3-yl)-(Z)-2-Fluoromethoxyiminoacetate

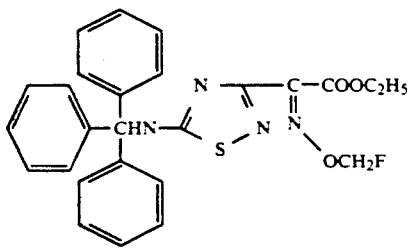

Ethyl 2-(5-tritylamino-1,2,4-thiadiazol-3-yl)-(Z)-2-hydroxyiminoacetate (60.4 g) was dissolved in dimethyl sulfoxide (210 ml). Potassium carbonate (96.48 g) was added under ice cooling, followed by stirring for 10 minutes. Bromofluoromethane (19 g) was added further, followed by stirring at room temperature for 3 hours. The reaction mixture was added with ethyl acetate (1 l) and washed with water and then with saturated saline. Anhydrous magnesium sulfate was added to the thus-washed reaction mixture to dry the same. The solvent was distilled off, and ethanol (120 ml) was added to the residue. Deposited crystals were collected by filtration and then washed with ethanol to obtain the target product (58.2 g). Infrared spectrum (cm$^{-1}$, Nujol) 1735, 1530.

NMR spectrum ($\delta$DMSO-d$_6$): 1.19(3H, t, J=7Hz), 4.21(2H, q, J=7Hz), 5.79(2H, d, J=55Hz), 7.30(15H, s), 10.03(1H, s).

EXPERIMENT 2

2-(5-Tritylamino-1,2,4-Thiadiazol-3-yl)-(Z)-2-Fluoromethoxyiminoacetic Acid

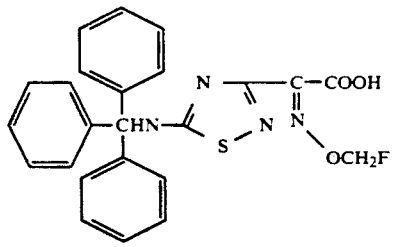

To a liquid mixture of sodium hydroxide (2.04 g), ethanol (146 ml) and water (29 ml) was added the compound (17.87 g) of Experiment 1. The resulting mixture was stirred for 20 minutes under reflux. After concentration of the reaction mixture under reduced pressure, ethyl acetate (200 ml) and 1N hydrochloric acid (77 ml) were added. The ethyl acetate layer was separated, and washed with saturated saline. Anhydrous magnesium sulfate was added to the thus-washed ethyl acetate layer to dry the same. The solvent was distilled off to obtain crystals. The crystals were added with petroleum ether, ground and then collected by filtration, thereby obtaining the target product (16.55 g).

Melting point: 144-146° C.

Mass spectrum (m/e) M$^+$+1 ... 463.

|  | C | H | N | F |
|---|---|---|---|---|
| Calculated (%): | 61.14 | 4.28 | 11.88 | 4.03 |
| Found (%): | 61.30 | 4.37 | 11.61 | 3.91 |

Infrared spectrum (cm$^{-1}$, Nujol): 1720, 1585.

NMR spectrum ($\delta$, DMSO-d$_6$): 5.78(2H, d, J=55Hz), 7.31(15H, s), 10.06(1H, s).

EXPERIMENT 3

2-(5-Tritylamino-1,2,4-thiadiazol-3-yl)-(Z)-2-fluoromethoxyiminoacetic acid chloride hydrochloride

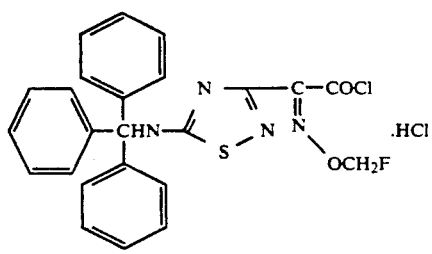

Phosphorus pentachloride (395 mg) was dissolved in dichloromethane (2.9 ml) and the resulting mixture was cooled to −5° C. The compound (627 mg) of Experiment 2 was added to the solution, followed by stirring at the same temperature for two and a half hours. The reaction mixture was added to a mixed solvent of n-hexane (9.4 ml) and n-octane (9.4 ml). Resulting crystals were collected by filtration and then washed with n-octane to obtain the target product (325 mg).

Melting point: 139-140° C. (decomposed).

Mass spectrum (m/e): M$^+$+1 ... 480($^{35}$Cl), 482($^{37}$Cl).

Infrared spectrum (cm$^{-1}$ Nujol) 1795, 1780, 1740, 1630.

NMR spectrum ($\delta$, DMSO-d$_6$): 5.79(2H, d, J=54Hz), 7.31(15H, s), 10.09(1H, s).

EXPERIMENT 4

Ethyl 2-(5-amino-1,2,4-thiadiazol-3-yl)-(Z)-2-fluoromethoxyiminoacetate

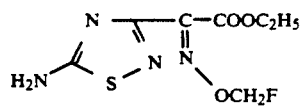

The compound (2.00 g) of Experiment 1 was stirred at room temperature for 30 minutes in trifluoroacetic acid. The solvent was distilled off and the residue was purified by chromatography on a silica gel column, thereby obtaining the target product (405 mg).

Melting point: 172-173° C.

Infrared spectrum (cm$^{-1}$, Nujol) 1730, 1615.

NMR spectrum ($\delta$, DMSO-d$_6$): 1.28(3H, t, J=7.0Hz), 4.34(2H, q, J=7.0Hz), 5.83(2H, d, J=54.5Hz), 8.27(2H, br).

EXPERIMENT 5

2-(5-Amino-1,2,4-Thiadiazol-3-yl)-(Z)-2-Fluoromethoxyiminoacetic Acid

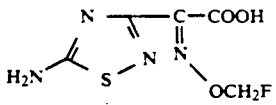

The compound (200 mg) of Experiment 4 was suspended in a mixed solvent of ethanol (6 ml) and water (2 ml), followed by an addition of a 1N aqueous solution of sodium hydroxide (1.75 ml). The resulting mixture was stirred at 60° C. for 1 hour. Ethanol was distilled off from the reaction mixture, and the residue was adjusted to pH 2 with 1N hydrochloric acid. The residue was then purified by means of "Dia-Ion SP207" (trade name for non-ionic adsorption resin, product of Mitsubishi Chemical Industries, Ltd.) to obtain the target product (30 mg).

Infrared spectrum (cm$^{-1}$, Nujol): 1720, 1620.

NMR spectrum ($\delta$DMSO-d$_6$): 5.76(2H, d, J=55.8Hz), 8.12(2H, br).

EXPERIMENT 6

2-Cyano-2-fluoromethoxyiminoacetamide

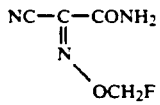

2-Cyano-2-hydroxyiminoacetamide (22.6 g) was dissolved in dimethyl sulfoxide (100 ml). Potassium carbonate (55.2 g) was added under stirring at room temperature, followed by stirring for further 20 minutes. Thereafter, a solution of fluorobromomethane (27 g) in dimethylformamide (20 ml) was added. The resulting mixture was stirred for 20 hours at room temperature and then allowed to cool down. The reaction mixture was added to ice water (1 l), followed by extraction twice with 150 ml of ethyl acetate. The organic layer was washed twice with saturated saline. Anhydrous magnesium sulfate was added to the thus-washed organic layer to dry the same. The solvent was thereafter distilled off. The residue was washed with ethyl ether and dried to obtain the target product (14.4 g).

Melting point: 124–125° C.

Infrared spectrum (cm$^{-1}$, Nujol): 3410, 3290, 3150, 1690, 1590.

NMR spectrum ($\delta$, DMSO-d$_6$): 5.94(2H, d, J=54.0Hz), 7.85–9.40(2H, br).

EXPERIMENT 7

2-Fluoromethoxyiminopropanedinitrile

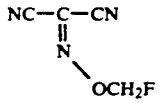

A mixture of the compound (14.0 g) of Experiment 6, acetonitrile (15 ml), sodium chloride (15 g) and phosphoryl chloride (14 ml) was reacted for 2 hours under reflux. Phosphoryl chloride (5 ml) was added further. They were reacted for additional 2 hours. After cooling the reaction mixture, it was added to ice water (200 ml) and the resulting mixture was stirred for 1 hour at room temperature. The mixture was then extracted twice with 50 ml of methylene chloride. The extract was washed with a 5% aqueous solution of sodium bicarbonate and then with saturated saline. After adding anhydrous magnesium sulfate to the thus-washed extract and drying the same, the solvent was distilled off. An oily product was distilled under reduced pressure, thereby obtaining the target product (9.1 g) in a colorless oily form.

Boiling point: 69–70° C./25 mmHg.

NMR spectrum ($\delta$, CDCl$_3$): 5.85(2H, d, J=52.0Hz).

EXPERIMENT 8

2-Cyano-2-fluoromethoxyiminoacetoamidine

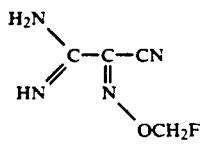

A liquid mixture of 28% aqueous ammonia (50 ml), ammonium chloride (8 g) and ethanol (50 ml) was cooled to −5° C., to which the compound (9.1 g) of Experiment 7 was added under stirring. The resulting mixture was stirred for additional 3 hours at the same temperature. Water (100 ml) was added to the reaction mixture, followed by extraction three times with methylene chloride (50 ml). After adding anhydrous magnesium sulfate to the extract and drying the same, the solvent was distilled off. The residue was washed with ethyl ether and then dried to obtain the target product (3.4 g).

In addition, a portion of the reaction product was dissolved in ethanol, followed by a dropwise addition of glacial acetic acid under stirring. The resulting precipitate was collected by filtration, washed with ethanol and then dried to obtain the acetate of the title compound. The following physical data are those of the acetate.

Melting point: 125–127° C. dec.

Infrared spectrum (cm$^{-1}$, Nujol): 3200, 1670, 1560.

NMR spectrum ($\delta$, DMSO-d$_6$): 1.90(3H, s), 5.95(2H, d, J=54.0Hz), 7.40(3H, br).

EXPERIMENT 9

2-(5-Amino-1,2,4-thiadiazol-3-yl)-(E)-2-fluoromethoxyiminoacetonitrile

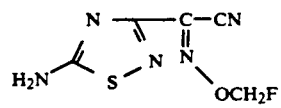

The compound (3.0 g) of Experiment 8 was dissolved in methanol (50 ml), followed by an addition of triethylamine (4.2 g) under ice cooling. After cooling the solution to −5° C., bromine (3.5 g) was added dropwise. Thereafter, a solution of potassium thiocyanate (2.1 g) in methanol was added dropwise at −3° C. to −5° C., and the resulting mixture was stirred for 2 hours at the same temperature. The resulting precipitate was collected by filtration and then washed with water and methanol. The precipitate thus washed was recrystallized from acetone to obtain the target product (3.4 g).

Melting point: 236–238° C. dec.

Infrared spectrum (cm$^{-1}$, Nujol): 3450, 3250, 3075, 1610, 1520.

NMR spectrum (δ, DMSO-d$_6$): 6.02(2H, d, J=54.0Hz), 8.38(2H, br).

EXPERIMENT 10

2-(5-Amino-1,2,4-thiadiazol-3-yl)-(Z)-2-fluoromethoxyiminoacetamide

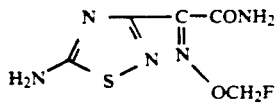

35% Hydrogen peroxide solution (7.4 ml) was added to an aqueous solution (18 ml) of sodium hydroxide (0.23 g). Under stirring at room temperature, the compound (2.0 g) of Experiment 9 was added, followed by stirring for 8 hours at 25° C. to 30° C. Deposited crystals were collected by filtration, washed with water and acetone and then dried, thereby obtaining the target product (1.3 g).

Melting point: 210–211° C. dec.

Infrared spectrum (cm$^{-1}$, Nujol) 3450, 3260, 3180, 1690, 1610.

NMR spectrum (δ, DMSO-d$_6$) 5.73(2H, d, J=55.0Hz), 7.69(2H, br), 7.98(1H, br), 8.10(1H, br).

EXPERIMENT 11

2-(5-Amino-1,2,4-Thiadiazol-3-yl)-(Z)-2-Fluoromethoxyiminoacetic Acid

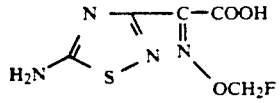

A mixture of the compound (1.1 g) of Experiment 10 and 10 ml of a 2N aqueous solution of sodium hydroxide (10 ml) was stirred at 50° C. for 5 hours. The reaction mixture was cooled, adjusted to pH 1.0 with concentrated hydrochloric acid, and then extracted three times with ethyl acetate (20 ml). After adding anhydrous magnesium sulfate to the extract and drying the same, the solvent was distilled off. The residue was washed with isopropyl ether to obtain a crude product (0.8 g). It was purified by reversed chromatography on a silica gel column, thereby obtaining the target product (0.4 g).

Its infrared spectrum and NMR spectrum were consistent with those obtained in Experiment 5.

EXPERIMENT 12

N-Fluoromethoxyphthalimide

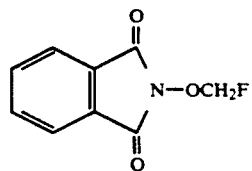

N-hydroxyphthalimide (80 g) and bromofluoromethane (63.2 g) were added to dry dimethyl sulfoxide (350 ml) which had been cooled to 0° C. Potassium carbonate (135 g) was added further, followed by stirring at room temperature for 4 hours. Thereafter, nitrogen gas was introduced for 1 hour. The reaction mixture was added to ice water (800 ml), followed by extraction three times with ethyl acetate (500 ml). After washing the extract with saturated saline, anhydrous magnesium sulfate was added to the extract to dry the same. The solvent was distilled off under reduced pressure. Deposited crystals were washed with isopropyl ether and petroleum ether to obtain the target product (55 g).

Melting point: 126–127° C.

Mass spectrum (m/e): M$^+$... 195.

Infrared spectrum (cm$^{-1}$, Nujol) 1785, 1730, 1700, 1600.

NMR spectrum (δ, CDCl$_3$): 5.64(2H, d, J=54.0Hz), 7.60–7.95(4H, m).

EXPERIMENT 13

Fluoromethoxyamine and its hydrochloride

H$_2$NOCH$_2$F(·HCl)

a) Fluoromethoxyamine:

To a mixed solvent of ethanol (180 ml) and water (5.2 ml), the compound (20 g) of Experiment 12 and hydrazine monohydrate (5.39 g) were added. The resultant mixture was refluxed for 1 hour. The reaction mixture was cooled and the deposit was filtered off. The filtrate was distilled off and the target product was obtained as an ethanol solution, namely, the target product and ethanol were distilled together. Its NMR will be given below without peaks attributable to ethanol.

NMR spectrum (δ, CDCl$_3$): 5.29(2H, d, J=56.6 Hz), 5.85–6.20(2H, br).

b) Fluoromethoxyamine hydrochloride:

A 1 mole solution (200 ml) of hydrogen chloride in ethanol was added to the ethanol solution of fluoromethoxyamine, which had been obtained in the above procedure a). Under reduced pressure, ethanol was distilled off. Ethanol and ethyl ether were added to the residue to crystallize the same. Resulting crystals were collected by filtration and then dried to obtain the target product (5 g).

Melting point: 152–154° C.

Mass spectrum (m/e): M$^+$... 101($^{35}$Cl), 103($^{37}$Cl).

NMR spectrum (δ, DMSO-d$_6$): 5.73(2H, d, J=54Hz), 10.80–11.25(3H, br).

EXPERIMENT 14

2-(5-Amino-1,2,4-Thiadiazol-3-yl)-(Z)-2-Fluoromethoxyiminoacetic Acid

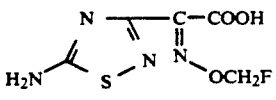

To a mixture of a solution of fluoromethoxyamine (0.58 g) in ethanol (25 ml) and water (0.45 ml), 2-(5-amino-1,2,4-thiadiazol-3-yl)-2-oxoacetic acid (1 g) was added. After adjusting the pH of the resulting mixture to 4–5 with a 10% aqueous solution of sodium hydroxide, the mixture was stirred overnight at room temperature. The solvent was distilled off under reduced pressure, water (20 ml) and sodium chloride (10 g) were added, and the pH of the solution was adjusted to 1 with concentrated hydrochloric acid. The solution was extracted four times with ethyl acetate (30 ml). After washing the extract with saturated saline, anhydrous magnesium sulfate was added to the extract to dry the same. The solvent was distilled off and the residue was crystallized from a 1:3 mixture of acetone and isopropyl ether, thereby obtaining the target product (0.38 g).

Its infrared spectrum and NMR spectrum were consistent with those of Experiment 5.

EXPERIMENT 15

2-(5-Tritylamino-1,2,4-Thiadiazol-3-yl)-(Z)-2-Fluoromethoxyiminoacetic Acid

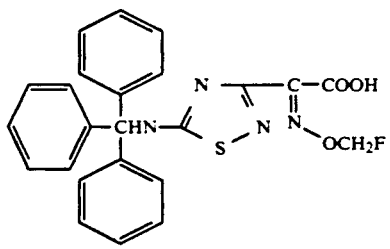

2-(5-Tritylamino-1,2,4-thiadiazol-3-yl)-2-oxoacetic acid (1 g) was added to a mixture of a solution of fluoromethoxyamine (0.58 g) in ethanol (25 ml) and water (0.45 ml). After adjusting the pH of the resulting mixture to 4-5 with a 10% aqueous solution of sodium hydroxide, the mixture was stirred overnight at room temperature. The solvent was distilled off under reduced pressure, followed by addition of water (20 ml) and sodium chloride (10 g) to the residue. The pH of the resulting solution was adjusted to 1 with concentrated hydrochloric acid. The solution was extracted four times with ethyl acetate (30 ml). After washing the extract with saturated saline, anhydrous magnesium sulfate was added to the extract to dry the same. The dry was distilled off and the residue was crystallized from a 1:10 mixture of acetone and isopropyl ether, thereby obtaining the target product (0.55 g).

Its infrared spectrum and NMR spectrum were consistent with those of Experiment 2.

EXPERIMENT 16

2-(5-Amino-1,2,4-thiadiazol-3-yl)-(Z)-2-fluoromethoxyiminoacetic acid

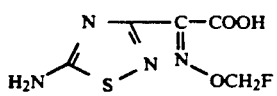

Added to trifluoroacetic acid (100 ml) was 2-(5-tritylamino-1,2,4-thiadiazol-3-yl)-(Z)-2-fluoromethoxyiminoacetic acid (13 g). The resulting mixture was stirred at room temperature for 24 hours. Trifluoroacetic acid was distilled off under reduced pressure. Water (100 ml) was added to the residue and an insoluble matter was filtered off. The solvent was distilled off from the filtrate under reduced pressure. The residue was crystallized from a 1:3 mixture of acetone and isopropyl ether, thereby obtaining the target product (2.18 g) as white crystals.

Its infrared spectrum and NMR spectrum were consistent with those of Experiment 5.

EXPERIMENT 17

2-(N-Chloro)Amidino-2-Fluoromethoxyiminoacetonitrile

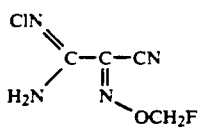

2-Amidino-2-fluoromethoxyiminoacetonitrile acetate (2.04 g) was dissolved in methanol (30 ml), followed by ice cooling. 3N hydrochloric acid (24 ml) was added to a liquid mixture of a 5% aqueous solution (60 ml) of sodium hypochlorite and ethyl ether (30 ml). The ethyl ether layer was separated to obtain an ethyl ether solution (30 ml) of hypochlorous acid. The ethyl ether solution (30 ml) of hypochlorous acid was added dropwise to the above solution under stirring. Five minutes later, the solvent was distilled off under reduced pressure. After adding a saturated aqueous solution (30 ml) of sodium bicarbonate, the resulting mixture was extracted three times with ethyl acetate (30 ml). The extract was washed with saturated saline. Anhydrous magnesium sulfate was added to the thus-washed extract to dry the same. The solvent was distilled off under reduced pressure to obtain crystals. The crystals were washed with petroleum ether and isopropyl ether to obtain the target product (1.72 g).

Melting point: 97–98° C.

Mass spectrum (m/e): M+... 178($^{35}$Cl), 180($^{37}$Cl).

Infrared spectrum (cm$^{-1}$, Nujol): 3470, 3330, 1630, 1570.

NMR spectrum (δ, DMSO-d$_6$): 5.97(2H, d, J=54Hz), 7.69(2H, br).

EXPERIMENT 18

2-(N-chloro)Amidino-2-Fluoromethoxyiminoacetic Acid

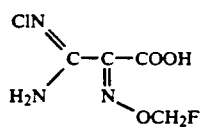

85% sodium peroxide (1.1 g) was dissolved in water (20 ml), followed by ice cooling. The resulting solution was added with the compound (1 g) of Experiment 17, followed by stirring for 3 hours. The mixture was stirred further at room temperature for 24 hours. The reaction mixture was ice-cooled, added with sodium chloride(10 g), and then adjusted to pH 1 with 6N hydrochloric acid. The mixture was thereafter extracted four times with ethyl acetate (20 ml). Anhydrous magnesium sulfate was added to the extract to dry the same. The solvent was distilled off under reduced pressure. Isopropyl ether and petroleum ether were added to the residue (oil) to solidify the same, thereby obtaining the target product (350 mg).

Melting point: 112–114° C. (decomposed).

Infrared spectrum (cm$^{-1}$, Nujol) 3300, 3150, 2650, 1720, 1590.

NMR spectrum (δDMSO-d$_6$): 5.79(2H, d, J=54Hz)

EXPERIMENT 19

2-(5-Amino-1,2,4-Thioadiazol-3-yl)-(Z)-2-Fluoromethoxyiminoacetic Acid

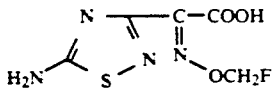

A liquid mixture of potassium thiocyanate (50 mg), triethylamine (127 mg) and methanol (3 ml) was cooled to −10° C. The compound (99 mg) of Example 18 was added to the mixture, followed by stirring at the same temperature for 1 hour and then at room temperature for 20 hours. The solvent was distilled off under reduced pressure, the residue was added with saturated saline (5 ml), and the resulting mixture was adjusted to pH 1 with 1N hydrochloric acid. The mixture was extracted four times with ethyl acetate (10ml). Anhydrous magnesium sulfate was added to the extract to dry the same, followed by extraction of the solvent under reduced pressure 2-Butanone and isopropyl ether were added to the residue to solidify the same, thereby obtaining the target product (56 mg).

Its infrared spectrum and NMR spectrum were consistent with those of Experiment 5.

EXPERIMENT 20

2-(5-Amino-1,2,4-Thiadiazol-3-yl)-(Z)-2-Fluoromethoxyiminoacetic Acid Chloride Hydrochloride

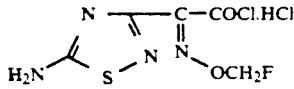

Phosphorus pentachloride (500 mg) was dissolved in dry methylene chloride (5 ml). After cooling the resulting solution to −10° C., 2-(5-amino-1,2,4-thidiazol-3-yl)-(Z)-2-fluoromethoxyiminoacetic acid (325 mg) was added and the resulting mixture was stirred at the same temperature for 30 minutes. Isopropyl ether (20 ml) was added to the reaction mixture, and the resulting precipitate was collected by filtration to obtain the target product (130 mg).

Mass spectrum (m/e) $M^+$ ... 238($^{35}Cl$), 240($^{37}1$).
Infrared spectrum (cm$^{-1}$, Nujol) 1780, 1625.
NMR spectrum ($\delta$DMSO-d$_6$): 5.85(2H, d, J=55Hz).

EXAMPLE 1

2-Ethylmethylaminoacetamide

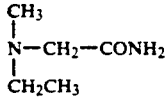

Water (37.5 ml) was added to ethylmethylamine (12.5 g), followed by addition of a 35% aqueous solution of formaldehyde (20.17 g) and sodium cyanide (10.98 g). After stirring the resulting mixture for 1 hour concentrated hydrochloric acid (21.1 ml) was added dropwise over 1 hour. The mixture was then allowed to cool down to room temperature, at which it was stirred overnight. The reaction mixture was extracted with chloroform (300 ml), and anhydrous magnesium sulfate was added to the extract to dry the same. The solvent was distilled off to obtain an oily substance of a pale yellow color.

Sulfuric acid (50 ml) was added at −20° C. to the oily substance. The resulting mixture was allowed to cool down to room temperature and then stirred for 2 days. The reaction mixture was added to ice water (200 ml), followed by neutralization with concentrated aqueous ammonia. After adding sodium chloride to saturation, the mixture was extracted with chloroform (3 l). Anhydrous magnesium sulfate was added to the extract to dry the same. The solvent was distilled off and the residue was recrystallized from benzene/petroleum ether, thereby obtaining the target product (12.7 g) as white needle crystals.

Melting point: 71-72° C.
Infrared spectrum (cm$^{-1}$, Nujol): 1610.
NMR spectrum ($\delta$DMSO-d$_6$): 0.98(3H, t, J=7.2Hz), 2.16(3H, s), 2.38(2H, q, J=7.2Hz), 2.79(2H, s), 7.03(2H, br).
Mass spectrum (m/e) 116(M$^+$)

EXAMPLE 2

(R)-2-Dimethylamino-3-Hydroxypropionamide

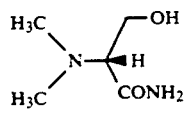

D-serine amide trifluoroacetate (9.0 g) was dissolved in water (12.6 ml). Under ice cooling, sodium bicarbonate (3.47 g) was added, followed by stirring for 10 minutes. The resulting mixture was added with acetonitrile (66.6 ml) to form a suspension. Under cooling at −5° C., were added a 37% aqueous solution (7.37 g) of formaldehyde and sodium cyanoborohydride (1.74 g), followed by stirring for 1 hour. An insoluble matter deposited was filtered off and the filtrate was concentrated under reduced pressure. The residue was purified by chromatography on a column packed with alumina (450 g), thereby obtaining the target product (3.4 g).

Mass spectrum (m/e): 132(M$^+$+1).
Infrared spectrum (cm$^{-1}$, Nujol): 3350, 1670, 1025.
NMR spectrum ($\delta$, DMSO-d$_6$): 2.20(6H, s), 2.78(1H, t, J=9Hz), 3.44–3.70(2H, m), 4.46(1H, br), 6.96(1H, br), 7.14(1H, br).

EXAMPLE 3

1-Aza-5-methyl-4,6-dioxabicyclo[3,3,1]nonane

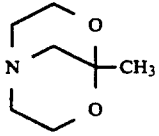

Diethanol amine (57.4 g) was dissolved in tetrahydrofuran (400 ml). Bromoacetone (41.5 g) was added dropwise to the resulting solution, followed by stirring for 5 hours. The lower layer was removed, and the solvent of the upper layer was distilled off. Ethyl acetate was added to the residue and an oily precipitate was removed. Thereafter, the solution was caused to pass through anhydrous magnesium sulfate to filter the same. The solvent was distilled off from the filtrate and the residue was subjected to crystallization in a cold place.

Petroleum ether was added, followed by collection of crystals by filtration. The target product (34.2 g) was obtained as colorless prismatic crystals.

Melting point: 65–67° C.

Mass spectrum (m/e): 143(M+)

NMR spectrum (δ, DMSO-d6): 1.36(3H, s), 2.05–2.9(6H, m), 3.5–4.2(4H, m).

EXPERIMENT 21 p-Methoxybenzyl 7β-(2-phenylacetamido)-3-triphenylphosphoniomethyl-3-cephem-4-carboxylate iodide

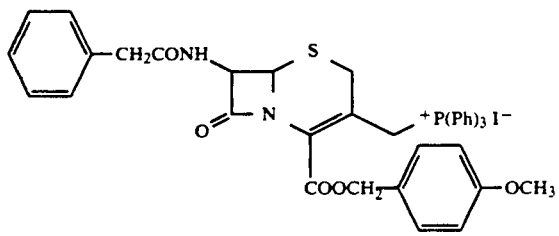

p-Methoxybenzyl 7β-(2-phenylacetamido)-3-chloromethyl-3-cephem-4-carboxylate (250 g) was suspended in acetone (1.5 l), followed by addition of triphenylphosphine (200 g) and sodium iodide (78 g). The resulting mixture was stirred at room temperature for 1 hour. An insoluble matter was filtered off and the filtrate was added dropwise under stirring to a mixed solvent of ethyl acetate (6 l) and isopropyl ether (3 l). A precipitate formed was collected by filtration. The precipitate was washed with isopropyl ether (600 ml) and then dried to obtain the target product (420 g).

Infrared spectrum (cm$^{-1}$, Nujol): 1780, 1710, 1670, 1610.

NMR spectrum (δ, DMSO-d6): 3.50(2H, s), 3.71(3H, s), 4.3–5.3(5H, m), 5.56(1H, dd, J=5.2Hz, 7.2Hz), 6.82(2H, d, J=8.0Hz), 7.0–7.4(7H, m), 7.4–8.0(15H, m), 9.00(1H, d, J=7.5Hz).

EXPERIMENT 22 p-Methoxybenzyl 7β-(2-Phenylacetamido)-3-[(Z)-3-Chloro-1-Propenyl]-3-Cephem-4-Carboxylate

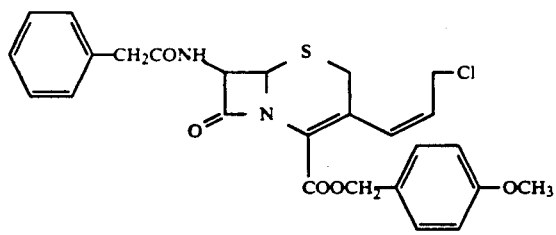

The compound (120 g) of Experiment 21 was dissolved in chloroform (0.8 l), followed by addition of a 1N aqueous solution of sodium hydroxide (223 ml) and saturated saline (200 ml). The resulting mixture was stirred. The organic layer was separated and washed with water. It was then dried with potassium carbonate. Potassium carbonate was removed and under ice cooling, N,O-bis(trimethylsilyl)acetamide (18.4 ml) was added. The resulting mixture was stirred for 5 minutes. A chloroform solution (150 ml) containing chloroacetaldehyde (67 g) was added, followed by stirring for 30 minutes. The solution was concentrated under reduced pressure and the residue was purified by chromatography on a silica gel column to obtain the target product (32.4 g).

Infrared spectrum (cm$^{-1}$, Nujol) 1760, 1720, 1660, 1610.

NMR spectrum (δ, DMSO-d6): 3.55(2H, s), 3.76(3H, s), 3.93(1H, dd, J=8.0Hz, 12.0Hz), 4.16(1H, dd, J=8.0Hz 12.0Hz), 5.14(2H, ABq, J=12.0Hz), 5.21(1H, d, J=5.0Hz), 5.70(1H, dt, J=11.3Hz, 8Hz), 5.74(1H, dd, J=5.0Hz, 8.0Hz), 6.30(1H, d, J=11.3Hz), 6.94(2H, d, J=8.5Hz), 7.28(5H, s), 7.33(2H, d, J=8.5Hz), 9.14(1H, d, J=8.0Hz).

EXPERIMENT 23 p-Methoxybenzyl 7β-Amino-3-[(Z)-3-Chloro-1-Propenyl]-3-Cephem-4-Carboxylate Hydrochloride

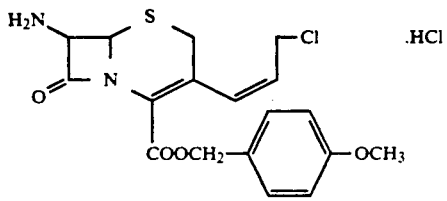

Pyridine (3.15 ml) was added to a solution (100 ml) of phosphorus pentachloride (8.12 g) in methylene chloride, followed by cooling to −15° C. The compound (10 g) of Experiment 22 was added, followed by stirring for one and a half hours. 1,3-Butanediol (20.9 ml) was added dropwise to the mixture, followed by stirring at −10° C. for 30 minutes. The reaction mixture was washed with 20% saline. Anhydrous magnesium sulfate was added to the reaction mixture to dry the same. The solution was concentrated and ethyl acetate (100 ml) was then added. A precipitate formed was collected by filtration to obtain the target product (5.0 g).

Infrared spectrum (cm$^{-1}$, Nujol): 1785, 1720, 1610, 1585.

NMR spectrum (δDMSO-d6): 3.75(3H, s), 3.85–4.3(2H, m), 5.05–5.45(4H, m), 5.55–5.9(1H, m), 6.35(1H, d, J=11.5Hz), 6.92(2H, d, J=8.5Hz), 7.32(2H, d, J=8.5Hz).

EXPERIMENT 24 p-Methoxybenzyl 7β-(2-Phenylacetamido)-3-[(E)-3-Iodo-1-Propenyl]-3-Cephem-4-Carboxylate

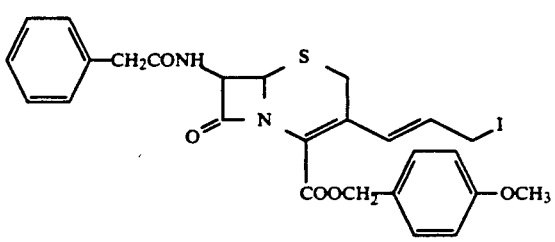

The compound (200 g) of Experiment 22 was dissolved in dry acetone (2.5 l, followed by an addition of sodium iodide (290 g). The resulting mixture was stirred at room temperature for 3 hours. The solution was concentrated. Deposited crystals were collected by filtration, and washed with a dilute aqueous solution of sodium thiosulfate, with water and then with acetone to obtain the target product (133.4 g).

Infrared spectrum (cm$^{-1}$, Nujol): 1775, 1715, 1650.

NMR spectrum (δ, DMSO-d$_6$): 3.50(1H, d, J=13.8Hz), 3.56(1H, d, J=13.8Hz), 3.59(1H, d, J=17.8Hz), 3.74(3H, s), 3.90(1H, d, J=17.8Hz), 4.30(2H, d, J=7.0Hz), 5.15(1H, d, J=4.8Hz), 5.19(1H, d, J=12.0Hz), 5.23(1H, d, J=12.0Hz), 5.70(1H, dd, J=4.8Hz, 8.4Hz), 6.22(1H, dt, J=15.4Hz, 7Hz), 6.79(1H, d, J=15.4Hz), 6.93(2H, d, J=8.4Hz), 7.2-7.35(5H, m), 7.36(2H, d, J=8.4Hz), 9.18(1H, d, J=8.4Hz).

EXAMPLE 4 p-Methoxybenzyl 7β-(2-Phenylacetamido)-3-[(E)-3-(1-Aza-5-Methyl-4,6-Dioxabicyclo[3,3,1]-Nonan-1-io)-1-Propenyl]-3-Cephem4-Carboxylate Iodide

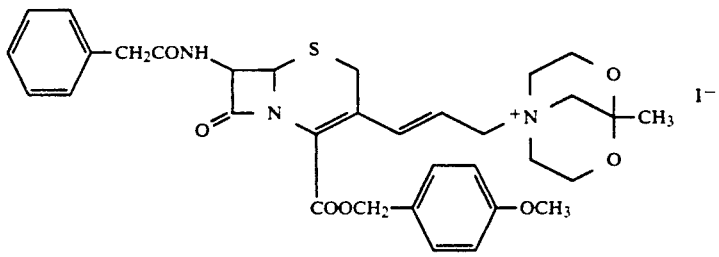

The compound (20 g) of Experiment 24 was suspended in N,N-dimethylformamide (75 ml), followed by an addition of the compound (7.07 g) of Example 3. The resulting mixture was stirred for 3 hours at room temperature, to which isopropyl ether (400 ml) and chloroform (100 ml) were added. The solution was added to a 5:1 mixture of ethyl ether and isopropyl ether (1.2 l), and a precipitate formed was collected by filtration. The precipitate was collected by filtration. It was then washed with ethyl acetate to obtain the target compound(20.0 g).

Infrared spectrum (cm$^{-1}$, Nujol): 1770, 1715, 1650.

NMR spectrum (δ, DMSO-d$_6$): 1.38(3H, s), 3.1-4.4(14H, m), 3.55(2H, s), 3.74(3H, s), 5.05-5.45(3H, m), 5.73(1H, dd, J=5.0Hz, 8.0Hz), 6.1-6.45(1H, m), 6.96(2H, d, J=8.5Hz), 7.30(5H, s), 7.38(2H, d, J=8.5Hz), 9.14(1H, d, J=8.0Hz).

EXAMPLE 5:

7β-(2-Phenylacetamido)-3-[(E)-3-(1-Aza-5-Methyl-4,6-Dioxabicyclo[3,3,1]Nonan-1-io)-1-Propenyl]-3-Cephem-4-Carboxylate Trifluoroacetate

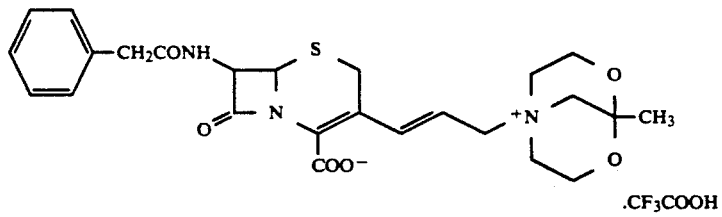

The compound (20.0 g) of Example 4 was suspended in anisole (100 ml). After dropwise addition of trifluoroacetic acid (120 ml) over 45 minutes under ice cooling; the resulting mixture was stirred for 1 hour. Isopropyl ether (1 l) was added to the reaction mixture and the resulting precipitate was collected by filtration. The precipitate was washed with ethyl acetate and ethyl ester to obtain the target product (13.1 g).

Infrared spectrum (cm$^{-1}$, Nujol): 1760, 1650.

NMR spectrum (δ, DMSO-d$_6$): 1.31(3H, s), 3.1-4.5(16H, m), 5.13(1H, d, J=5.4Hz), 5.69(1H, dd, J=5.4Hz 8.1Hz), 6.07-6.40(1H, m), 7.09(1H, d, J=15.3Hz), 7.09-7.60(5H, s), 9.15(1H, d, J=8.1 Hz).

EXAMPLE 6

7β-Amino-3-[(E)-3-(1-Aza-5-Methyl-4,6-Dioxabicyclo[3,3,1]Nonan-1-io)-1-Propenyl]-3-Cephem-4-Carboxylate Perchlorate

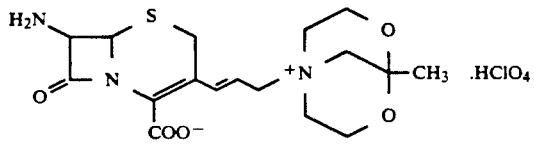

Sodium acetate trihydrate (5 g) and the compound (5 g) of Example 5 were dissolved in water (20 ml). Activated carbon (0.3 g) was added to the solution. After stirring the mixture at room temperature for 15 minutes, the mixture was filtered and the pH of the filtrate was adjusted to 8 with aqueous ammonia. To the solution thus prepared, was added "Carrier-Fixed Penicillin G Amidase" [trade name for penicillin G amidase derived from *Escherichia coli* (carrier: polyacrylamide); product of Boehringer Mannheim Yamanouchi K.K.] (2 g). While maintaining the pH of the solution within 7.5-8.0 with aqueous ammonia, the solution was stirred at the same temperature for one and a half hours. The solution was filtered, followed by filtration of the filtrate by chromatography on a column packed with "SEPA-BEADS SP207" (trade name for styrene-divinylbenzene copolymer based adsorbent; product of Mitsubishi Chemical Industries, Ltd.). Relevant fractions were concentrated to 10 ml. Perchloric acid (70%) was added to the concentrate to adjust its pH to 2-3. Isopropanol (60 ml) was added, and crystals thus formed were collected by filtration and then washed with acetone to obtain the target product (0.4 g) as yellow powder.

Infrared spectrum (cm$^{-1}$, Nujol): 1760, 1680, 1610.

NMR spectrum (δ, DMSO-d$_6$+D$_2$O): 1.34(3H, s), 3.22–4.36(14H, m), 4.81(1H, d, J=5.1 Hz), 5.04(1H, d, J=5.1 Hz), 5.86–6.30(1H, m), 7.10(1H, d, J=15.3Hz).

EXAMPLE 7 p-Methoxybenzyl 7β-(2-Phenylacetamido)-3-[(E)-3-((R)-1-Carbamoyl-2-Hydroxyethyl)dimethylammonio]-1-Propenyl]-3-Cephem-4-Carboxylate·Iodide In a similar manner as in Example 5 the compound (3.65 g) of Example 7 was suspended in anisole (22 ml) and then reacted with trifluoroacetic acid (25 ml) to obtain the target compound (2.67 g) as pale yellow powder.

Infrared spectrum (cm$^{-1}$, Nujol): 1770, 1680.

NMR spectrum (δ, DMSO-d$_6$): 3.11(3H, s), 3.17(3H, s), 3.52(2H, s), 3.6–4.4(7H, m), 5.11(1H, d, J=5.0Hz), 5.65(1H, dd, J=5.0Hz, 8.0Hz), 5.9–6.35(1H, m), 7.02(1H, d, J=15.3Hz), 7.23(5H, s), 7.77(1H, br), 8.09(1H, br), 9.09(1H, d, J=8.0Hz).

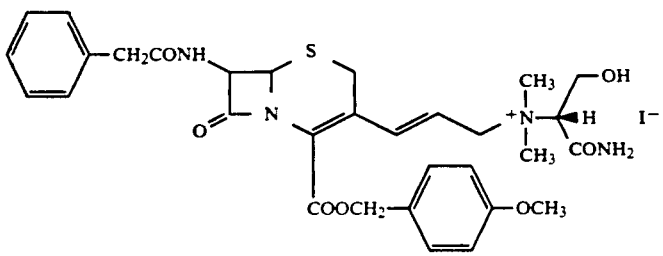

The compound (5.0 g) of Experiment 24 was suspended in N,N dimethylformamide (19 ml) and under ice cooling, (R)-2-dimethylamino-3-hydroxypropionamide (1.42 g) was added. The resulting mixture was stirred for 2 hours while allowing its temperature to rise gradually to room temperature. Isopropyl ether (200 ml) was added, followed by stirring. The supernatant was removed. Chloroform (80 ml) was added to the remaining oily precipitate to dissolve the same. Ethyl ether (300 ml) was added dropwise to the solution thus prepared. A precipitate thus occurred was collected by filtration to obtain the target product (3.89 g) as pale yellow powder.

Infrared spectrum (cm$^{-1}$, Nujol): 1775, 1690, 1655.

NMR spectrum (δ, DMSO-d$_6$): 3.11(3H, s), 3.17(3H, s), 3.52(2H, s), 3.73(3H, s), 3.85–4.1(3H, br), 4.1–4.35(2H, m), 5.15(1H, d, J=4.8Hz), 5.18(2H, s), 5.5–5.8(1H, br), 5.69(1H, dd, J=4.8Hz, 8.0Hz), 5.95–6.4(1H, m), 6.90(2H, d, J=8.5Hz), 7.23(5H, s), 7.32(2H, d, J=8.5Hz), 7.80(1H, br), 8.01(1H, br), 9.09(2H, d, J=8.0Hz).

EXAMPLE 8

7β-(2-Phenylacetamido)-3-[(E)-3-[((R)-1-Carbamoyl-2-Hydroxyethyl) Dimethylammonio]-1-Propenyl]-3-Cephem-4-Carboxylate Trifluoroacetate

EXAMPLE 9

7β-Amino-3-[(E)-3-[((R)-1-Carbamoyl-2-Hydroxy-Ethyl) Dimethylammonio]-1-Propenyl]-3-Cephem-4-Carboxylate Perchlorate

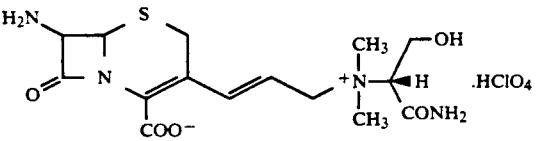

In a similar manner as in Example 6, the compound (8.0 g) of Example 8 was hydrolyzed using "Carrier-Fixed Penicillin G Amidase" (2 g) to obtain the target product (1.485 g) as pale yellow crystals.

Infrared spectrum (cm$^{-1}$, Nujol): 1775, 1690, 1585.

NMR spectrum (δ, DMSO-d$_6$): 3.11(3H, s), 3.18(3H, s), 3.4–4.1(5H, m), 4.25(2H, br d, J=6.8Hz), 4.89(1H, d, J=5.2Hz), 5.10(1H, d, J=5.2Hz), 5.9–6.3(1H, m), 7.06(1H, d, J=15.8Hz), 7.78(1H, br,) 8.15(1H, br).

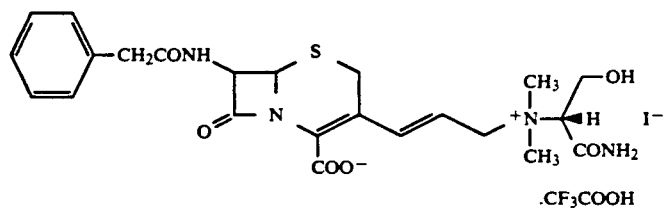

EXAMPLE 10

7β-[2-(5-Amino-1,2,4-Thiadiazol-3-yl)-(Z)-2-fluoromethoxyiminoacetamido]-3-[(E)-3-[((R)-1-Carbamoyl-2-Hydroxyethyl)Dimethylammonio]-1-propenyl]-3-Cephem-4-Carboxylate

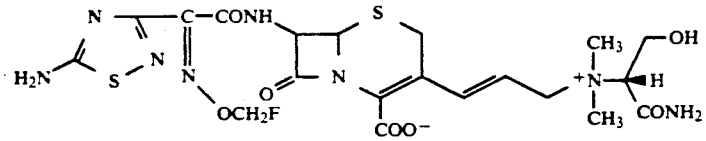

To a solution of sodium acetate trihydrate (230 g) in a mixed solvent of methanol (5.5 ml) and water (1 ml), were added the compound (150 mg) of Example 9 and the compound (100 mg) of Experiment 20. The resulting mixture was stirred for 1 hour at room temperature. Methanol was distilled off, and the residue was purified by chromatography on a silica gel column to obtain the target product (46 mg).

Infrared spectrum (cm$^{-1}$, Nujol): 1765, 1670, 1600, 1530.

NMR spectrum (δ, DMSO-d$_6$): 3.08(3H, s), 3.14(3H, s); 3.49(1H, d, J=17.2Hz), 3.62(1H, d, J=17.2Hz), 3.87(1H, dd, J=5.5Hz, 12.5Hz), 4.06(1H, dd, J=5.5Hz, 12.5Hz), 4.1–4.2(1H, m), 4.19(2H, d, J=7.3Hz), 5.08(1H, d, J=5.0Hz), 5.67(1H, dd, J=4.8Hz, 8.4Hz), 5.70–5.85(1H, m), 5.79(2H, d, J=55.0Hz), 7.11(1H, d, J=15.4Hz), 7.76(1H, s), 8.22(2H, s), 8.52(1H, s), 9.73(1H, d, J=8.4Hz).

| Antibacterial activities. MIC (μg/ml): | |
|---|---|
| Staphylococcus aureus 209-P | 0.2 |
| Escherichia coli NIHJ | ≦0.025 |
| Klebsiella pneumoniae EK-6 | ≦0.025 |
| Serratia marcescens ES-75 | ≦0.025 |
| Morganella morgani EP-14 | ≦0.025 |
| Pseudomonas aeruginosa EP-01 | 0.8 |

EXAMPLE 11 p-Methoxybenzyl 7β-(2-Phenylacetamido)-3-[(E)-3-(Carbamoylmethylethylmethylammonio)-1-Propenyl]-3-Cephem-4-Carboxylate-iodide

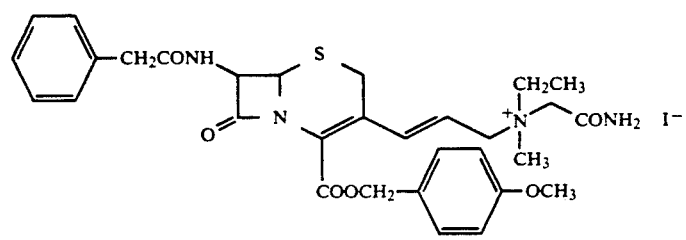

In a similar manner as in Example 4, the compound (20 g) of Experiment 24 was reacted with 2-ethylmethylaminoacetamide (4.22 g) to obtain the target product (23.0 g).

Infrared spectrum (cm$^{-1}$, Nujol): 1770, 1650.

NMR spectrum (δDMSO-d$_6$): 1.15–1.4(3H, m), 3.14(3H, s), 3.25–3.8 (4H, m), 3.55(2H, s), 3.77(3H, s), 4.0–4.2(4H, m), 5.16(1H, d, J=5.2Hz), 5.23(2H, s), 5.71(1H, dd, J=5.2Hz, 8.0Hz), 5.95–6.4(1H, m), 6.96(2H, d, J=8.8Hz), 7.30(5H, s), 7.41(2H, d, J=8.8Hz), 7.75(1H, br), 8.43(1H, br), 9.21(1H, d, J=8.0Hz).

EXAMPLE 12

7β-(2-Phenylacetamido)-3-[(E)-3-(Carbamoylmethylethylmethylammonio)-1-Propenyl]-3-Cephem-4-carboxylate trifluoroacetate

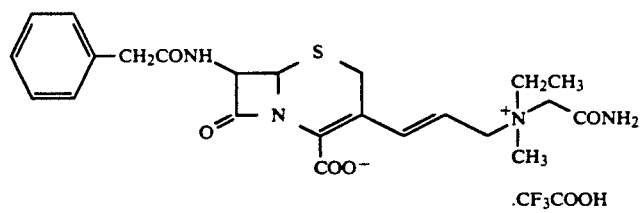

In a manner similar to Example 5, the compound (23 g) of Example 11 was suspended in anisole (130 ml), followed by an addition of trifluoroacetic acid (140 ml) to obtain the target product (15.9 g).

Infrared spectrum (cm$^{-1}$, Nujol): 1775, 1690.

NMR spectrum (δDMSO-d$_6$): 1.26(3H, br t, J=6.8Hz), 3.10(3H, s), 3.52(2H, s), 3.90–4.15(4H, m), 5.08(1H, d, J=4.8Hz), 5.62(1H, dd, J=4.8Hz, 8.0Hz), 5.9–6.4(1H, m), 6.97(1H, d, J=15.7Hz), 7.20(5H, s), 7.63(1H, br), 8.31(1H, br) 9.08(1H, d, J=8.0Hz).

EXAMPLE 13

7β-Amino-3-[(E)-3-(Carbamoylmethylethylmethylammonio)-1-Propenyl]-3-Cephem-4-Carboxylate Paratoluenesulfonate

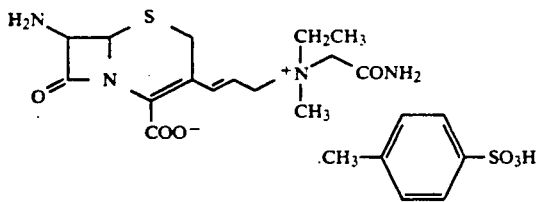

In a similar manner as in Example 6 except for the use of paratoluenesulfonic acid monohydrate in place of perchloric acid, the compound (5.9 g) of Example 12 was hydrolyzed using "Carrier-Fixed Penicillin G Amidase" (5.9 g) to obtain the target product (0.85 g).

Infrared spectrum (cm$^{-1}$, Nujol): 1770, 1690, 1590.
NMR spectrum (δDMSO-d$_6$): 1.25(3H, br t, J=6.5Hz), 2.26(3H, s), 3.07(3H, s), 3.3–4.05(6H, m), 4.18(2H, br d, J=6.8Hz), 4.77(1H, d, J=5.0Hz), 4.98(1H, d, J=5.0Hz), 5.8–6.2(1H, m), 6.97(1H, d, J=16Hz), 7.05(2H, d, J=8.0Hz), 7.43(2H, d, J=8.0Hz), 7.60(1H, br), 7.93(1H, br).

EXAMPLE 14

7β-[2-(5-Amino-1,2,4-Thiadiazol-3-yl)-(Z)-2-Fluoromethoxyiminoacetamido]-3-[(E)-3-(Carbamoylmethylethylmethylammonio)-1-Propenyl]-3-Cephem-4-Carboxylate

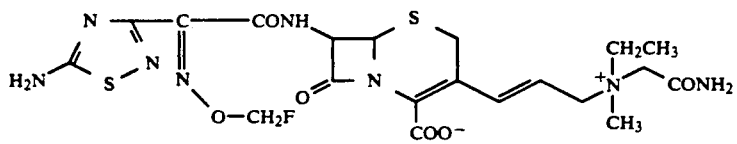

In a similar manner as in Example 10, the compound (60 mg) of Example 13 was reacted with the compound (32 mg) of Experiment 20 to obtain the target product (18 mg).

Infrared spectrum (cm$^{-1}$, Nujol): 1760, 1675, 1590, 1520.

NMR spectrum (δ, DMSO-d$_6$) 1.26(3H, t, J=7.2Hz), 3.08 and 3.09(together, 3H, s), 3.4–3.6(2H, m), 3.47(1H, d, J=16.8Hz), 3.65(1H, d, J=16.8Hz), 4.01(2H, s), 4.05–4.2(2H, m), 5.06(1H, d, J=4.8Hz), 5.6–5.75(2H, m), 5.79(2H, br d, J=55.3Hz), 7.17(1H, d, J=15.8Hz), 7.66(1H, s), 8.23(2H, s), 8.33(1H, s), 9.71(1H, d, J=8.4Hz).

| Antibacterial activities, MIC (μg/ml): | |
|---|---|
| Staphylococcus aureus 209-P | 0.2 |
| Escherichia coli NIHJ | ≦0.025 |
| Klebsiella pneumoniae EK-6 | ≦0.025 |
| Serratia marcescens ES-75 | 0.1 |
| Morganella morgani EP-14 | ≦0.025 |
| Pseudomonas aeruginosa EP-01 | 0.8 |

EXAMPLE 15 p-Methoxybenzyl 7β-(2-phenylacetamido)-3-[(E)-3-[((R)-1-Carbamoylethyl)Dimethylammonio]-1-propenyl]-3-cephem-4-carboxylate·iodide

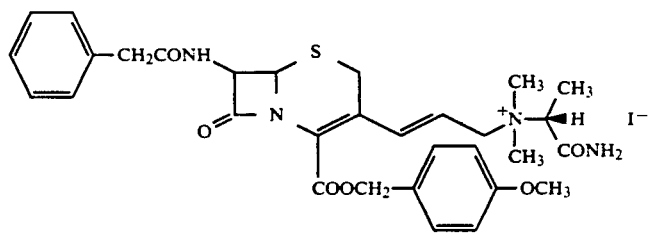

In a similar manner as in Example 4, the compound (30 g) of Experiment 24 was reacted with (R)-2-dimethylaminopropionamide (6.33 g) to obtain the target product (35.1 g).

Infrared spectrum (cm$^{-1}$, Nujol): 1775, 1690, 1658.
NMR spectrum (δ, DMSO-d$_6$) 1.48(3H, d, J=6.5Hz), 3.07(6H, s), 3.51(2H, s), 3.72(3H, s), 3.9–4.25(3H, m), 5.13(1H, d, J=5.2Hz), 5.16(2H, br), 5.67(1H, dd, J=5.2Hz, 7.2Hz), 5.9–6.3(1H, m), 6.87(2H, d, J=8.5Hz), 7.20(5H, s), 7.30(2H, d, J=8.5Hz), 7.69(1H, br), 7.87(1H, br), 9.04(1H, d, J=7.8Hz).

EXAMPLE 16

7β-(2-Phenylacetamido)-3-[(E)-3-[((R)-1-Carbamoylethyl)Dimethylammonio]-1-Propenyl]-3-Cephem-4-Carboxylate Trifluoroacetate

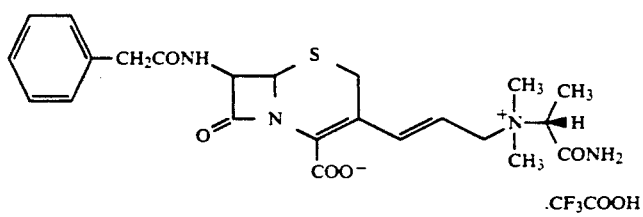

.CF$_3$COOH

In a similar manner as in Example 5, the compound (34.5 g) of Example 14 was suspended in anisole (210 ml), followed by an addition of trifluoroacetic acid (230 ml) to obtain the target compound (25.9 g).

Infrared spectrum (cm$^{-1}$, Nujol): 1775, 1685.

NMR spectrum (δ, DMSO-d$_6$): 1.50(3H, d, J=6.5Hz), 3.10(6H, s), 3.74(2H, s), 3.8–4.3(3H, m), 5.15(1H, d, J=5.0Hz), 5.70(1H, dd, J=5.0Hz, 7.8Hz), 5.9–6.35(1H, m), 7.06(1H, d, J=16.2Hz), 7.28(5H, s), 7.73(1H, br), 8.00(1H, br), 9.11(1H, d, J=7.8Hz).

EXAMPLE 17

7β-Amino-3-[(E)-3-((R)-1-Carbamoylethyl)-dimethylammonio]-1-propenyl]-3-Cephem-dimethylammonio]-1-propenyl]-3-cephem-4-carboxylate perchlorate

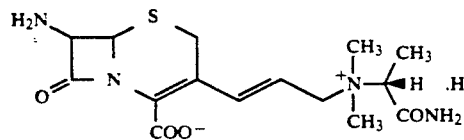

In a similar manner as in Example 6, the compound (3.3 g) of Example 16 was hydrolyzed using "Carrier-Fixed Penicillin G Amidase" (0.8 g) to obtain the target product (770 mg).

Infrared spectrum (cm$^{-1}$, Nujol): 1795, 1680, 1630, 1575.

NMR spectrum (δ, DMSO-d$_6$): 1.48(3H, d, J=6.2Hz), 3.24(6H, s), 3.53(1H, d, J=17.5Hz), 3.90(1H, d, J=17.5Hz), 4.76(1H, d, J=5.2Hz), 4.99(1H, d, J=5.2Hz), 5.8–6.2(1H, m), 6.98(1H, d, J=15.5Hz), 7.63(1H, br), 8.00(1H, br).

EXAMPLE 18

7β-[2-(5-Amino-1,2,4-Thiadiazol-3-yl)-(Z)-2-Fluoromethyoxyiminoacetamido]-3-[(E)-3-[((R)-1Carbamoylethyl)dimethylammonio]-1-propenyl]-3-Cephem-4-Carboxylate

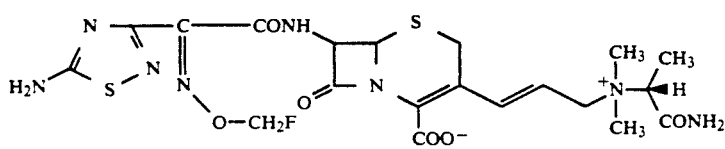

In a similar manner as in Example 10, the compound (120 mg) of Example 16 was reacted with the compound (75 mg) of Experiment 20 to obtain the target product (30 mg).

Infrared spectrum (cm-1, Nujol): 1760, 1670, 1590, 1520.

NMR spectrum (δ, DMSO-d$_6$): 1.46(3H, d, J=7.0Hz), 3.04(3H, s), 3.06(3H, s), 3.49(1H, d, J=17.2Hz), 3.64(1H, d, J=17.2Hz), 4.05(1H, m), 4.15–4.30(2H, m), 5.09(1H, d, J=5.0Hz), 5.67(1H, dd, J=5.0Hz, 8.0Hz), 5.5–5.8(1H, m), 5.79(2H, brd, J=55.5Hz), 7.18(1H, d, J=15.4Hz), 7.67(1H, s), 8.21(2H, s), 8.64(1H, s), 9.70(1H, d, J=8.0Hz).

| Antibacterial activities, MIC (μg/ml): | |
|---|---|
| *Staphylococcus aureus* 209-P | 0.2 |
| *Escherichia coli* NIHJ | ≦0.025 |
| *Klebsiella pneumoniae* EK-6 | ≦0.025 |
| *Serratia marcescens* ES-75 | 0.1 |
| *Morganella morgani* EP-14 | ≦0.025 |
| *Pseudomonas aeruginosa* EP-01 | 1.56 |

EXAMPLE 19 p-Methoxybenzyl 7β-(2-Phenylacetamido)-3-[(E)-3-(Carbamoylmethyldiethylammonio)-1-Propenyl]-3-Cephem-4-Carboxylate-iodide

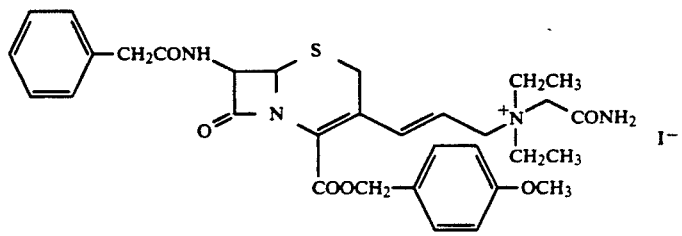

In a similar manner as in Example 4, the compound (20 g) of Experiment 24 was reacted with N,N-diethylglycine amide (5.15 g) to obtain the target product (17.5 g).

Infrared spectrum (cm$^{-1}$, Nujol): 1765, 1675, 1600.

NMR spectrum (δ, DMSO-d$_6$): 1.22(6H, m), 3.24-3.62(8H, m), 3.72(3H, s), 3.90(2H, m), 4.18(2H, m), 5.08-5.28(3H, m), 5.66(1H, dd, J=5.1 Hz, 8.4Hz), 5.86-6.40(1H, m), 6.8-7.0(3H, m), 7.20(5H, br), 7.29(2H, d, J=8.5Hz), 7.68(1H, br), 7.88(1H, br), 9.05(1H, d, J=8.4Hz).

EXAMPLE 20

7β-(2-Phenylacetamido)-3-[(E)-3-(Carbamoylmethydiethylammonio)-1-Propenyl]-3-Cephem-4-carboxylate trifluoroacetate

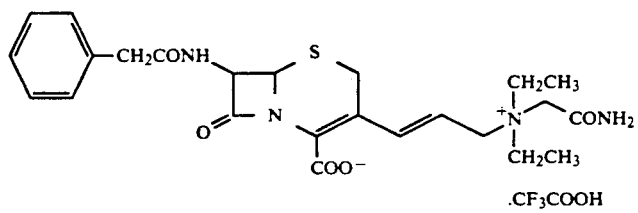

In a manner similar to Example 5, the compound (16.5 g) of Example 19 was suspended in anisole (82.5 ml), followed by an addition of trifluoroacetic acid (99 ml) to obtain the target product (11.8 g).

Infrared spectrum (cm$^{-1}$, Nujol): 1765, 1675.

NMR spectrum (β, DMSO-d$_6$): 1.24(6H, t, J=7Hz), 3.3-3.7(8H, m), 3.90(2H, br), 4.0-4.3(2H, m), 5.08(1H, d, J=5.4Hz), 5.63(1H, dd, J=5.4Hz, 7.2Hz), 5.80-6.30(1H, m), 6.98(1H, d, J=15.4Hz), 7.12-7.32(5H, s), 7.62(1H, s), 7.88(1H, s), 9.02(1H, d, J=7.2Hz).

EXAMPLE 21

7β-Amino-3-[(E)-3-(Carbamoylmethyldiethylammonio)-1-Propenyl]-3-Cephem-4-Carboxylate Perchlorate

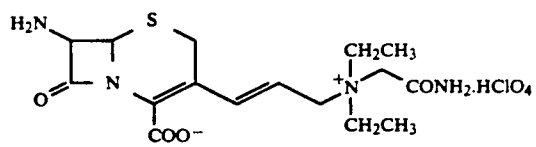

In a similar manner as in Example 6, the compound (5 g) of Example 20 was hydrolyzed using "Carrier-Fixed Penicillin G Amidase" (2 g) to obtain the target product (0.82 g).

Infrared spectrum (cm$^{-1}$, Nujol): 1770, 1680, 1600.

NMR spectrum (δ, DMSO-d$_6$+D$_2$O): 1.24(6H, m), 3.2-3.7(6H, m), 3.86(2H, br), 4.0-4.3(2H, m), 4.78(1H, d, J=5.1 Hz), 4.99(1H, d, J=5.1 Hz), 5.78-6.28(1H, m), 6.98(1H, d, J=15.4Hz), 7.64(1H, br), 7.90(1H, br).

EXPERIMENT 25 p-Methoxybenzyl 7β-Formamido-3-(Triphenylphosphonio)methyl-3-Cephem-4-Carboxylate-iodide

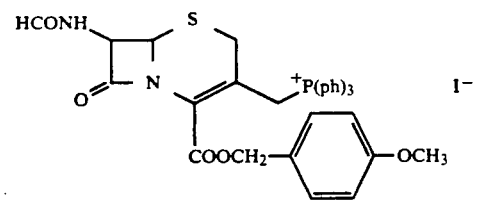

p-Methoxybenzyl 7β-formamido-3-iodomethyl-3-cephem-4-carboxylate (50 g) was dissolved in ethyl acetate (2.5 l), followed by an addition of triphenylphosphine (40.3 g). The resulting mixture was stirred at room temperature for 6 hours. A precipitate thus formed was collected by filtration and then washed with ethyl acetate and isopropyl ether to obtain the target product (56 g).

Infrared spectrum (cm$^{-1}$, Nujol): 1770, 1710, 1650.

NMR spectrum (δ, DMSO-d$_6$): 3.42(1H, dd, J=2Hz, 18Hz), 3.55(1H, dd, J=5Hz, 18Hz), 3.76(3H, s), 4.61(1H, d, J=12Hz), 4.82(1H, d, J=12Hz), 4.91(1H, dd, J=16Hz, 16Hz), 5.17(1H, dd, J=16Hz, 16Hz), 5.23(1H, d, J=4.5Hz), 5.73(1H, dd, J=4.5Hz, 8Hz), 6.90(2H, d, J=8.8Hz), 7.17(2H, d, J=8.8Hz), 7.70-7.93(15H, m), 8.13(1H, s), 9.03(1H, d, J=8Hz).

EXPERIMENT 26 p-Methoxybenzyl 7β-Formamido-3-[(Z)-3-Chloro-1-Propenyl]-3-Cephem-4-Carboxylate

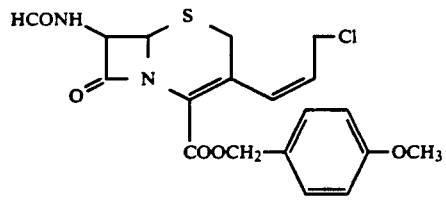

The compound (5 g) of Experiment 25 was dissolved in chloroform (30 ml), followed by addition of a 1N aqueous solution of sodium hydroxide (20 ml) and saturated saline (10 ml). The resulting mixture was stirred for 5 minutes. The organic layer was separated and dried over anhydrous magnesium sulfate. N,O-bis(-trimethylsilyl)acetamide (1.32 ml) and a 56% solution (1.9 g) of chloroacetaldehyde in chloroform were thereafter added under ice cooling, followed by stirring for 1 hour. Silica gel (15 g) was added to the reaction mixture. After stirring the mixture for 1 minute, silica gel was filtered off. The filtrate was concentrated and ethyl acetate (20 ml) was added to the residue. A solution thus prepared was added dropwise to isopropyl ether (50 ml) under stirring. Deposited crystals were collected by filtration and dried to obtain the target product (440 mg).

Infrared spectrum (cm$^{-1}$, Nujol) 1780, 1725, 1655.

NMR spectrum ($\delta$, DMSO-d$_6$): 3.29(1H, d, J=18.0Hz), 3.54(1H, d, J=18.0Hz), 3.71(1H, dd, J=8.0Hz, 12.0Hz), 3.78(3H, s), 3.96(1H, dd, J=8.0Hz, 12.0Hz), 5.00(1H, d, J=5.0Hz), 5.13(2H, s), 5.71(1H, dt, J=11.5Hz, 8.0Hz), 5.86(1H, dd, J=5.0Hz, 8.0Hz), 6.23(1H, d, J=11.5Hz), 6.44(1H, brd, J=8.0Hz), 6.83(2H, d, J=9.0Hz), 7.27(2H, d, J=9.0Hz), 8.22(1H, s).

EXPERIMENT 27 p-Methoxybenzyl 7β-Formamido-3-[(Z)-3-Chloro-1-Propenyl]-3-Cephem-4-Carboxylate

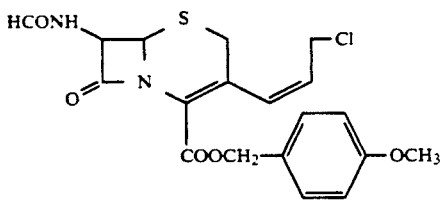

The compound (50 g) of Experiment 23 was suspended in ethyl acetate (700 ml), followed by a dropwise addition of N,O-bis(trimethylsilyl)acetamide under ice cooling. The temperature of the resulting mixture was allowed to rise to room temperature, at which it was stirred for 2 hours. An insoluble matter was filtered off. Formic acid (17.5 ml) and glacial acetic acid (44 ml) were heated at 50° C. for 30 minutes. Thereafter, the resulting solution was allowed to cool down to room temperature. The solution was added to the filtrate under ice cooling and the resulting mixture was allowed to stand overnight. Deposited crystals were collected by filtration and then washed with a 1:1 mixture of isopropyl ether and ethyl acetate to obtain the target product (42.9 g).

Its infrared spectrum and NMR spectrum were consistent with those of Experiment 26.

EXPERIMENT 28 p-Methoxybenzyl 7β-Formamido-3-[(E)-3-Iodo-1-Propenyl]-3-Cephem-4-Carboxylate

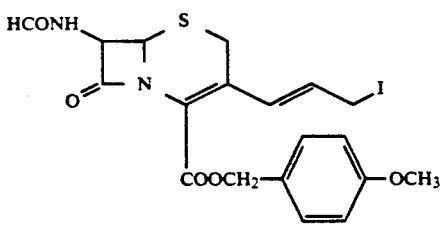

The compound (21 g) of Experiment 27 was dissolved in acetone (700 ml), followed by an addition of sodium iodide (37.2 g) under ice cooling. The resulting mixture was stirred at the same temperature for 30 minutes and then at room temperature for 3 hours. The solvent was distilled off, followed by an addition of ethyl acetate (500 ml). The resulting mixture was washed three times with a dilute aqueous solution of sodium thiosulfate and then with saturated saline, and thereafter dried over anhydrous magnesium sulfate. After concentrating the solution, ethyl ether and isopropyl ether were added. A precipitate thus formed was collected by filtration to obtain the target product (12.8 g).

Infrared spectrum (cm$^{-1}$, Nujol): 1770, 1710, 1645.

NMR spectrum ($\delta$, CDCl$_3$): 3.43(1H, d, J=18.0Hz), 3.62(1H, d, J=18.0Hz), 3.77(3H, s), 3.94(2H, d, J=8.0Hz), 4.93(1H, d, J=5.0Hz), 5.17(2H, s), 5.82(1H, dd, J=5.0Hz, 9.0Hz), 6.08(1H, dt, J=15.8Hz, 8.0Hz), 6.43(1H, d, J=9.0Hz), 6.84(2H, d, J=8.5Hz), 6.93(1H, d, J=15.8Hz), 7.29(2H, d, J=8.5Hz), 8.19(1H, s).

EXAMPLE 22 p-Methoxybenzyl 7β-Formamido-3-[(E)-3-((R)-1-Carbamoylethyl)Dimethylammonio]1-Propenyl]-3-Cephem-4-Carboxylate-iodide

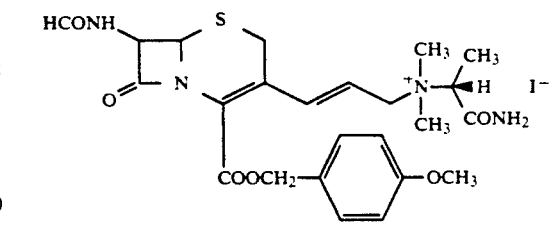

A mixture of the compound (3 g) of Experiment 28, N,N-dimethylformamide (12 ml) and (R)-2-dimethylaminopropionamide (900 ml) was stirred for 3 hours under ice cooling. Ethyl ether was added to the reaction mixture, followed by removal of the supernatant. Ethyl acetate was added for solidification. After adding ethyl ether, the thus-solidified product was collected by filtration to obtain the target product (2.83 g).

Infrared spectrum (cm$^{-1}$Nujol) 1780, 1690.

NMR spectrum ($\delta$, DMSO-d$_6$): 1.50(3H, d, J=6.5Hz), 3.08(6H, s), 3.73(3H, s), 3.85-4.3(3H, m), 5.0-5.35(3H, m), 5.81(1H, dd, J=5.0Hz, 8.0Hz), 5.9-6.4(1H, m), 6.89(2H, d, J=8.5Hz), 7.33(2H, d, J=8.5Hz), 7.74(1H, br), 7.93(1H, br], 8.10(1H, s), 9.05(1H, d, J=8.0Hz).

EXAMPLE 23

7β-Formamido-3-[(E)-3-[((R)-1-Carbamoylethyl)Dimethylammonio]-1-Propenyl]-3-Cephem-4-carboxylate trifluoroacetate

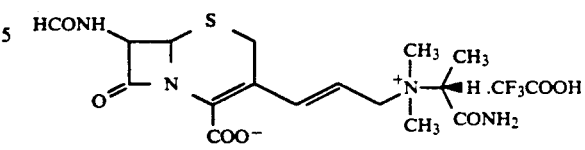

In a similar manner as in Example 5 the compound (0.8 g) of Example 22 was suspended in anisole (5 ml), followed by an addition of trifluoroacetic acid (6 ml) to obtain the target compound (0.56 g).

Infrared spectrum (cm$^{-1}$, Nujol): 1775, 1685.

NMR spectrum ($\delta$, DMSO-d$_6$): 1.48(3H, d, J=6.5Hz), 3.07(6H, s), 3.5-4.3(5H, m), 5.16(1H, d, J=5.0Hz), 5.77(1H, dd, J=5.0Hz, 8.5Hz), 5.9-6.35(1H, m), 7.02(1H, d, J=15.5Hz), 7.70(1H, br), 7.96(1H, br), 8.09(1H, s), 9.04(1H, d, J=8.5Hz).

EXAMPLE 24

7β-Amino-3-[(E)-3-[((R)-1-Carbamoylethyl)Dimethylammonio]-1-Propenyl]-3-Cephem-4-Carboxylate Hydrochloride

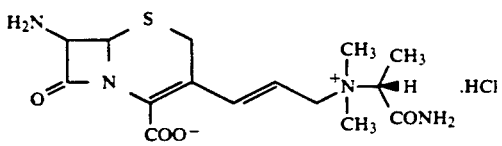

The compound (0.5 g) of Example 23 was dissolved at room temperature in a 4% (w/v) hydrochloric acid-methanol solution (5 ml), followed by stirring for 1 hour. Acetonitrile (50 ml) was added, and a precipitate thus formed was collected by filtration. The precipitate was washed with acetonitrile and acetone to obtain the target product (0.31 g). Infrared spectrum (cm$^{-1}$, Nujol): 1780, 1690.

NMR spectrum (δ, DMSO-d$_6$): 1.48(3H, d, J=6.5Hz), 3.12(6H, s), 3.4–4.6(5H, m), 5.18(1H, d, J=5.2Hz), 5.24(1H, d, J=5.2Hz), 6.1–6.55(1H, m), 7.08(1H, d, J=15.8Hz), 7.68(1H, br), 8.68(1H, br).

EXAMPLE 25 p-Methoxybenzyl 7β-Formamido-3-[(E)-3-(Carbamoylmethylethylmethylammonio)-1-Propenyl]-3-Cephem-4-carboxylate-iodide

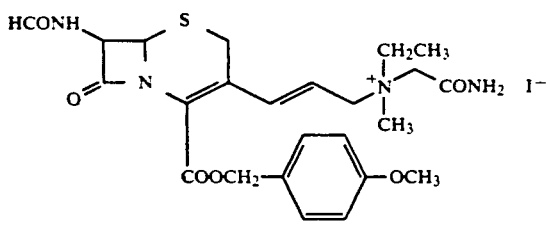

In a similar manner as in Example 22, the compound (3 g) of Experiment 28 and 2-ethylmethylaminoacetamide (0.9 g) were reacted to obtain the target product (3.53 g).

Infrared spectrum (cm$^{-1}$m Nujol): 1775, 1690.

NMR spectrum (δ, DMSO-d$_6$): 1.25(3H, br t, J=6.5Hz), 3.09(3H, s); 3.3–3.8(4H, m), 3.73(3H, s), 3.93(2H, br), 4.1–4.35(2H, m), 5.10(1H, d, J=11.5Hz), 5.21(1H, d, J=4.8Hz), 5.24(1H, d, J=11.5Hz), 5.79(1H, dd, J=4.8Hz, 8.5Hz), 5.9–6.35(1H, m), 6.88(2H, d, J=8.7Hz), 7.31(2H, d, J=8.7Hz), 7.67(1H, br), 7.86(1H, br), 8.09(1H, s), 9.03(1H, d, J=8.5Hz).

EXAMPLE 26:

7β-Formamido-3-[(E)-3-(Carbamoylmethylethylmethylammonio)-1-Propenyl]-3-Cephem-4-Carboxylate trifluoroacetate

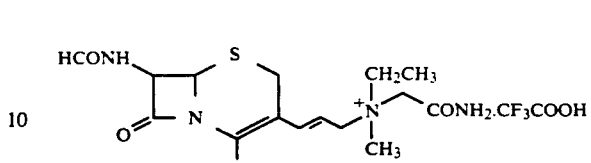

In a similar manner as in Example 5, the compound (3.4 g) of Example 25 was suspended in anisole (20 ml), followed by an addition of trifluoroacetic acid (23 ml) to obtain the target compound (2.04 g).

Infrared spectrum (cm$^{-1}$, Nujol): 1775, 1680.

NMR spectrum (δ, DMSO-d$_6$): 1.25(3H, br t, J=6.5Hz), 3.09(3H, s), 3.3–3.9)4H, m), 3.95(2H, br), 4.05–4.4(2H, m), 5.15(1H, d, J=5.0Hz), 5.74(1H, dd, J=5.0Hz, 8.5Hz), 5.9–6.3(1H, m), 7.00(1H, d, J=15.3Hz), 7.64(1H, br), 7.91(1H, br), 8.09(1H, s), 9.05(1H, d, J=8.5Hz).

EXAMPLE 27

7δ-Amino-3-[(E)-3-(Carbamoylmethylethylmethylammonio)-1-Propenyl]-3-Cephem-4-Carboxylate hydrochloride

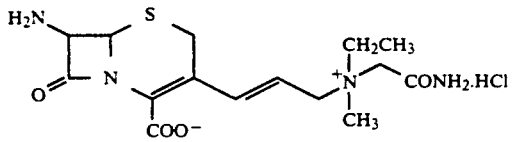

In a similar manner as in Example 24, the compound (1.97 g) of Example 26 was stirred in a 4% (w/v) hydrochloric acid-methanol solution (20 ml) to obtain the target product (1.25 g).

Infrared spectrum (cm$^{-1}$, Nujol): 1780, 1685.

NMR spectrum (δ, DMSO-d$_6$): 1.28(3H, br), 3.13(3H, s), 3.3–4.4(6H, m), 4.11(2H, br), 5.19(2H, br), 6.0–6.5(1H, m), 7.06(1H, d, J=15.0Hz), 7.68(1H, br), 8.37(1H, br).

EXAMPLE 28 p-Methoxybenzyl 7β-Formamido-3-[(E)-3-[((R)-1-Carbamoyl-2-Hydroxyethyl)Dimethylammonio]-1-Propenyl]-3-Cephem-4-Carboxylate

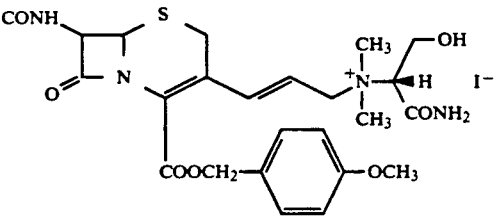

The compound (6.01 g) of Experiment 27 was dissolved in N,N-dimethylformamide (24 ml). (R)-2-dimethylamino-3-hydroxypropionamide (1.88 g) was added and the resulting mixture was stirred for 1 hour under ice cooling. Isopropyl ether (100 ml) was added to the reaction mixture, the supernatant was removed, and an oily precipitate thus obtained was dissolved in a mixed solvent of methanol (40 ml) and acetone (20 ml). The resulting solution was added dropwise to a mixed solvent of ethyl acetate (300 ml) and ethyl ether (150 ml). A precipitate thus formed was collected by filtration to obtain the target product (5.33 g).

Infrared spectrum (cm$^{-1}$, Nujol): 1775, 1680.

NMR spectrum (δ, DMSO-d$_6$): 3.11(3H, s), 3.16(3H, s), 3.73(3H, s), 4.00(3H, br), 4.25(2H, br d, J=6.5Hz), 5.0–5.3(3H, m), 5.60(1H, br), 5.80(1H, dd, J=5.0Hz, 8.5Hz), 6.0–6.4(1H, m), 6.89(2H, d, J=8.5Hz), 7.31(2H, d, J=8.5Hz), 7.78(1H, br), 8.00(1H, br), 8.10(1H, s), 9.05(1H, d, J=8.5Hz).

EXAMPLE 29

7β-Formamido-3-[(E)-3-[((R)-1-Carbamoyl-2-Hydroxyethyl)dimethylammonio]-1-Propenyl]-3-Cephem-4-Carboxylate Trifluoroacetate

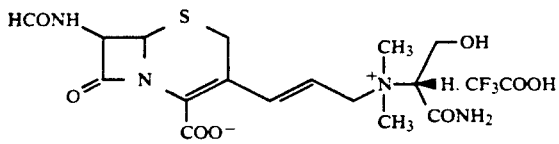

In a similar manner as in Example 5, the compound (4.98 g) of Example 28 was suspended in anisole (30 ml), followed by an addition of trifluoroacetic acid (33 ml) to obtain the target compound (4.03 g).

Infrared spectrum (cm$^{-1}$, Nujol) 1780, 1685.

NMR spectrum (δ, DMSO-d$_6$): 3.10(3H, s), 3.16(3H, s), 3.4–4.2(5H, m), 4.25(2H, br d, J=6.5Hz), 5.15(1H, d, J=5.0Hz), 5.77(1H, dd, J=5.5Hz, 8.5Hz), 5.9–6.35(1H, m), 7.00(1H, d, J=15.5Hz), 7.75(1H, br), 8.04(1H, br), 8.09(1H, s), 9.03(1H, d, J=8.5Hz).

EXAMPLE 30

7β-Amino-3-[(E)-3-[((R)-1-Carbamoyl-2-Hydroxyethyl)Dimethylammonio]-1-Propenyl]-3-Cephem-4-Carboxylate Hydrochloride

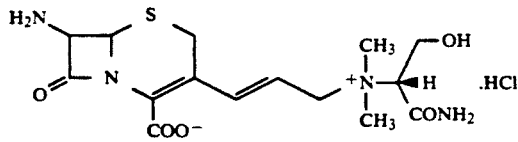

In a similar manner as in Example 24, the compound (4 g) of Example 29 was stirred in a 4% (w/w) hydrochloric acid-methanol solution (40 ml) to obtain the target product (2.57 g).

Infrared spectrum (cm$^{-1}$, Nujol): 1780, 1690.

NMR spectrum (δ, DMSO-d$_6$): 3.12(3H, s), 3.21(3H, s), 3.6–4.6(7H, m), 5.15(1H, d, J=5.0Hz), 5.23(1H, d, J=5.0Hz), 6.1–6.65(1H, m), 7.06(1H, d, J=15.5Hz), 7.76(1H, br), 8.67(1H, br).

EXPERIMENT 29 p-Methoxybenzyl 7β-(3-Nitrobenzylidene)amino-3-Chloromethyl-3-Cephem-4-Carboxylate

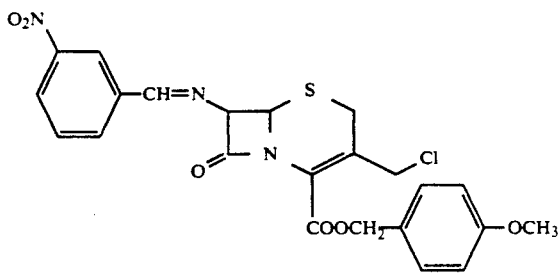

p-Methoxybenzyl 78-amino-3-chloromethyl-3-cephem-4-carboxylate hydrochloride (10 g) was suspended in chloroform (100 ml), followed by a dropwise addition of a 1N aqueous solution of sodium hydroxide (32 ml). The resulting mixture was stirred for 30 minutes at the same temperature. The organic layer was separated and washed with saturated saline. Anhydrous magnesium sulfate was then added to the organic solution to dry the same. 3-Nitrobenzaldehyde (4.08 g) was added to the solution, followed by stirring for 5 hours at room temperature. Isopropyl ether (0.5 l) and ethyl ether (0.5 l) were added to the reaction mixture, and a precipitate thus formed was collected by filtration to obtain the target product (8.0 g).

Infrared spectrum (cm$^{-1}$, Nujol): 1750, 1690, 1640, 1600.

NMR spectrum (δ, CDCl$_3$): 3.38(1H, d, J=18Hz), 3.67(1H, d, J=18Hz), 3.76(3H, s), 4.34(1H, d, J=11.7Hz), 4.54(1H, d, J=11.7Hz), 5.13(1H, d, J=5.4Hz), 5.20(2H, s), 5.42(1H, dd, J=1.8Hz, 5.4Hz), 6.84(2H, d, J=8.5Hz), 7.31(2H, d, J=8.5Hz), 7.44–8.52(4H, m), 8.61(1H, d, J=1.8Hz).

EXPERIMENT 30 p-Methoxybenzyl 7β-(3-Nitrobenzylidene)amino-3-Triphenylphosphoniomethyl-3-Cephem-4-Carboxylate-iodide

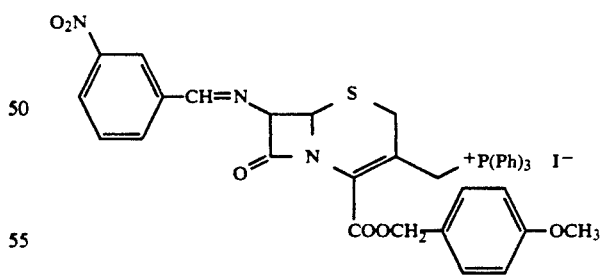

The compound (7.5 g) of Experiment 29 was suspended in acetone (80 ml), followed by addition of sodium iodide (2.7 g) and triphenylphosphine (4.7 g). The resulting mixture was stirred at room temperature for four and a half hours. The reaction mixture was filtered and the filtrate was added to a 3:1 mixture (800 ml) of ethyl acetate and isopropyl ether. A precipitate thus formed was collected by filtration to obtain the target product (12.3 g).

Infrared spectrum (cm$^{-1}$, Nujol) 1760, 1700, 1620, 1600.

NMR spectrum (δ, CDCl₃): 3.06(1H, br), 3.28(1H, br), 3.76(3H, s), 4.06-4.36(2H, m), 4.83(2H, s), 5.22(1H, d, J=4.5Hz), 5.41(1H, d, J=4.5Hz), 6.80(2H, d, J=8.5Hz), 7.17(2H, d, J=8.5Hz), 7.5-7.9(16H, m), 8.0-8.56(3H, m), 8.60(1H, br).

EXPERIMENT 31 p-Methoxybenzyl 7-(3-nitrobenzylidene)amino-3-(Z)-(3-chloropropenyl)-3-cephem-4-carboxylate

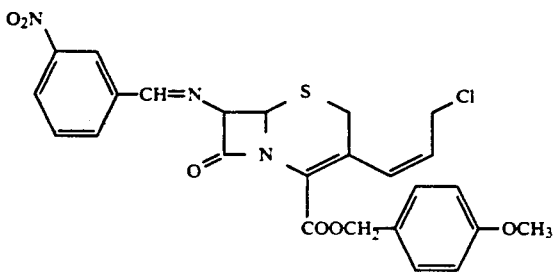

The compound (12.3 g) of Experiment 30 was dissolved in dichloromethane (200 ml), to which a 1N aqueous solution of sodium hydroxide (28 ml) was added. The resulting mixture was shaken. The organic layer was separated and then washed with saturated saline. Anhydrous magnesium sulfate was added to the organic solution to dry the same. After adding N,O-bis(-trimethylsilyl)acetamide (4.56 g) to the organic solution at 0° C, chloroacetaldehyde (3.3 g) in the form of a solution in chloroform was added dropwise over 30 minutes. After stirring the resulting mixture for 2 hours at the same temperature, silica gel (50 g) was added. Silica gel was filtered off. The filtrate was concentrated to 50 ml. The concentrate was added to isopropyl ether. A precipitate thus formed was collected by filtration and then washed with ethyl ether to obtain the target product (3.3 g).

Infrared spectrum (cm⁻¹, Nujol) 1760, 1700, 1630, 1600.

NMR spectrum (δ, CDCl₃): 3.35-3.75(2H, m), 3.76(3H, s), 3.76-4.12(2H, m), 5.14(2H, s), 5.20(1H, d, J=5.4Hz), 5.45(1H, dd, J=1.8Hz, 5.4Hz), 5.67(1H, dt, J=11.0Hz, 7.2Hz), 6.22(1H, d, J=11.0Hz), 6.83(2H, d, J=8.5Hz), 7.28(2H, d, J=8.5Hz), 7.45-8.56(4H, m), 8.63(1H, d, J=1.8Hz).

EXAMPLE 31 p-Methoxybenzyl 7β-(3-nitrobenzylidene)amino-3-[(E)-(3-carbamoylmethylethylmethylammonio)-1-propenyl)-3-cephem-4-carboxylate-iodide

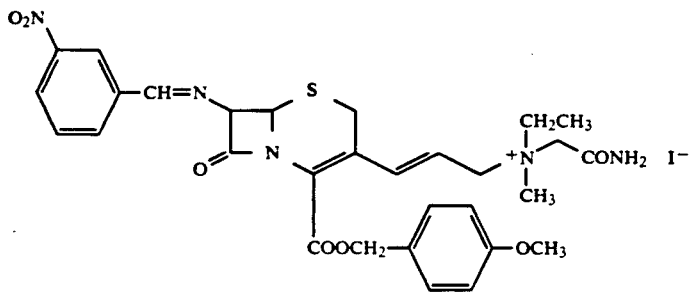

Acetone (10 ml) was added to the compound (3 g) of Experiment 31, followed by a dropwise addition of a solution of sodium iodide (2.56 g) in acetone (20 ml over 20 minutes. The resulting mixture was stirred for 3 hours. Ethyl acetate (80 ml) was added to the solution, followed by filtration. The filtrate was washed successively with a 10% aqueous solution of sodium thiosulfate and with saturated saline. Activated carbon and anhydrous magnesium sulfate were added to the thus-washed solution and the resulting mixture was stirred. After adding silica gel (30 g) further, the resulting mixture was filtered. The filtrate was concentrated to 30 ml, followed by a dropwise addition of a solution of N,N-ethylmethylglycine amide (792 mg) in ethyl acetate (30 ml) over 30 minutes. The resulting mixture was then stirred for 2 hours. Ethyl ether (50 ml) was added to the reaction mixture. A precipitate thus formed was collected by filtration and washed with ethyl acetate and ethyl ether to obtain the target product (2.0 g).

Infrared spectrum (cm⁻¹Nujol): 1760, 1680, 1600.

NMR spectrum (δ, DMSO-d₆): 1.26(3H, t, J=7.0Hz), 3.11(3H, s), 3.4-3.8(4H, m), 3.75(3H, s), 3.96(2H, br), 4.25(2H, m), 5.24-5.31(2H, m), 5.44(1H, d, J=5.1 Hz), 5.79(1H, br d, J=5.1 Hz), 6.0-6.3(1H, m), 6.8-7.0(3H, m), 7.37(2H, d, J=8.4Hz), 7.7-8.8(7H, m).

EXAMPLE 32

7β-Amino-3-[(E)-3-(carbamoylmethylethylmethylammonio)-1-propenyl]-3-cephem-4-carboxylate perchlorate

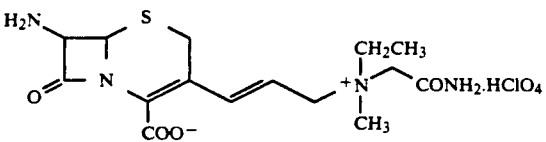

90% Formic acid (2.5 ml) was added to the compound (1 g) of Example 31, followed by an addition of 35% hydrochloric acid (0.5 ml) under ice cooling over 30 minutes. The resulting mixture was stirred at the same temperature for 30 minutes and then at room temperature for 1.5 hours. A small amount of activated carbon was added and then filtered off. The filtrate was added to acetone (450 ml), and a precipitate thus formed was collected by filtration. The precipitate was washed with acetone and ethyl ether to obtain the target product as its hydrochloride (0.41 g).

The hydrochloride was dissolved in water (20 ml), to which a small amount of activated carbon was added. After adjusting the pH of the resulting mixture to 7-8 with dilute aqueous ammonia, the mixture was filtered. The filtrate was purified by chromatography on a column packed with "SEPABEADS SP207". Relevant fractions were concentrated to 5 ml. The pH of the resulting concentrate was adjusted to 2-3 by adding 70% perchloric acid. Isopropanol (80 ml) was added. A precipitate thus formed was collected by filtration and then washed with acetone and ethyl ether to obtain the target product (0.15 g).

Its infrared spectrum and NMR spectrum were consistent with those of Example 21.

Hz), 5.20(2H, s), 5.29(1H, br d, J=5. 1 Hz), 5.96(2H, s), 6.70-7.40(7H, m), 8.36(1H, br).

EXPERIMENT 33 p-Methoxybenzyl 7β-(3,4-methylenedioxybenzylidene)amino-3-triphenylphosphoniomethyl-3-cephem-4-carboxylate·iodide

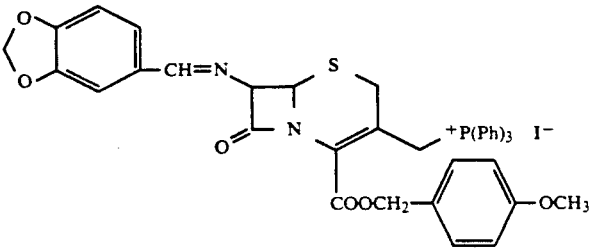

EXPERIMENT 32 p-Methoxybenzyl 7β-(3,4-methylenedioxybenzylidene)amino-3-chloromethyl-3-cephem-4-carboxylate

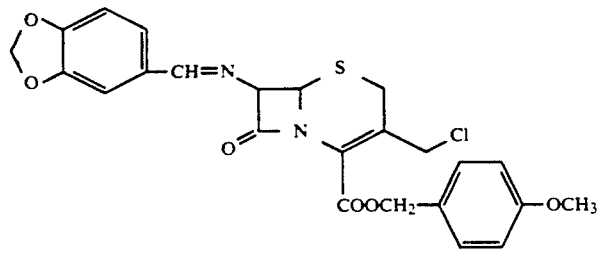

p-Methoxybenzyl 7β-amino-3-chloromethyl-3-cephem-4-carboxylate hydrochloride (10 g) was suspended in ethyl acetate (100 ml), followed by a dropwise addition of a 1N aqueous solution of sodium hydroxide (32 ml) under ice cooling. The resulting mixture was stirred at the same temperature for 30 minutes. The organic layer was separated, washed with saturated saline, and then dried over anhydrous magnesium sulfate. Piperonal (8.1 g) and chloroform (200 ml) were added, followed by overnight stirring at room temperature. The reaction mixture was concentrated to 50 ml, followed by an addition of ethyl ether (1 l). A precipitate thus formed was collected by filtration to obtain the target product (8.4 g).

Infrared spectrum (cm⁻¹, Nujol): 1760, 1700, 1620, 1590.

NMR spectrum (δ, CDCl₃): 3.34(1H, d, J=18.0Hz), 3.64(1H, d, J=18.0Hz), 3.76(3H, s), 4.35(1H, d, J=11.7Hz), 4.53(1H, d, J=11.7Hz), 5.06(1H, d, J=5.1

The compound (8 g) of Experiment 32 was suspended in acetone (80 ml), followed by an addition of sodium iodide (2.88 g) and triphenylphosphine (5.03 g). The resulting mixture was stirred for 2 hours at room temperature. The reaction mixture was filtered and the filtrate was added to a 2:1 mixture (900 ml) of ethyl acetate and ethyl ether. A precipitate thus formed was collected by filtration to obtain the target product (13 g).

Infrared spectrum (cm⁻¹, Nujol): 1760, 1700, 1620, 1590.

NMR spectrum (βCDCl₃): 2.9-3.3(2H, m), 3.77(3H, s), 4.04-4.38(2H, m), 4.85(2H, s), 5.13(1H, br d, J=4.5Hz), 5.96(2H, s), 6.73-7.84(22H, m), 8.35(1H, br).

EXPERIMENT 34 p-Methoxybenzyl 7β-(3,4-methylenedioxybenzylidene)amino-3-(Z)-(3-chloropropenyl)-3-cephem-4-carboxylate

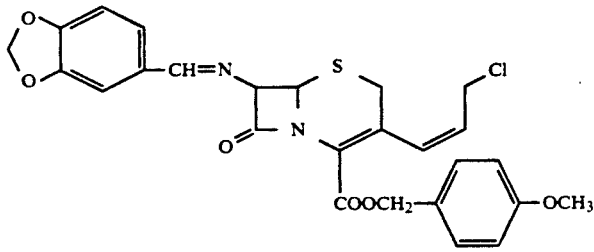

The compound (12 g) of Experiment 33 was dissolved in dichloromethane (100 ml), followed by an addition of a 1N aqueous solution of sodium hydroxide (28 ml). The resulting mixture was shaken. The organic layer was separated, washed with saturated saline, and then dried over anhydrous magnesium sulfate. N,O-Bis(trimethylsilyl)acetamide (5.7 g) was added at 0° C., to which chloroacetaldehyde (3.3 g) as a solution in chloroform was added dropwise over 30 minutes. The resulting mixture was stirred for 2 hours at the same temperature. Silica gel (75 g) was added and then filtered off. The filtrate was concentrated to 30 ml and then added to isopropyl ether (1 l). A precipitate thus formed was collected by filtration and then washed with ethyl ether to obtain the target product (3.7 g).

Infrared spectrum (cm$^{-1}$, Nujol) 1740, 1700, 1620, 1600.

NMR spectrum (δ, CDCl$_3$): 3.14–3.60(2H, m), 3.77(3H, s), 3.7–4.1(2H, m), 5.1–5.4(4H, m), 5.5–5.8(1H, m), 5.96(2H,s), 6.20(1H, d, J=10.8Hz), 6.7–7.4(7H, m), 8.37(1H, br).

EXAMPLE 33 p-Methoxybenzyl 7β-(3,4-methylenedioxybenzylidene)amino-3-[(E)-3-[((R)-1-carbamoylethyl)dimethylammonio]-1-propenyl]-3-cephem-4-carboxylate·iodide

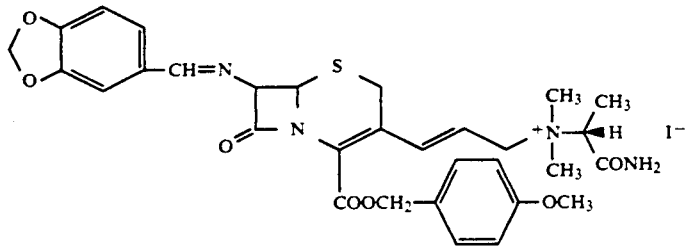

In a similar manner as in Example 31, the compound (3 g) of Experiment 34 and sodium iodide (1.28 g) were reacted, followed by a further reaction with (R)-2-dimethylaminopropionamide (661 mg) to obtain the target product (1.75 g).

Infrared spectrum (cm$^{-1}$, Nujol): 1760, 1680, 1620, 1590.

NMR spectrum (δ, DMSO-d$_6$): 1.50(3H, d, J=6.3Hz), 3.07(6H, br), 3.0–4.3(5H, m), 3.72(3H, s), 5.18(2H, br), 5.35(1H, d, J=5.4Hz), 5.63(1H, d, J=5.4Hz), 5.8–6.3(1H, m), 6.06(2H, s), 6.76–7.38(8H, m), 7.74(1H, br), 7.96(1H, br), 8.41(1H, br).

EXAMPLE 34

7β-Amino-3[(E)-3-[((R)-1-carbamoylethyl)dimethylammonio]-1-propenyl]-3-cephem-4-carboxylate perchlorate

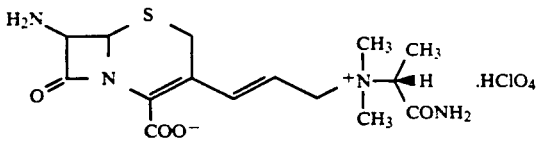

In a similar manner as in Example 32, the compound (1.65 g) of Example 33 was deprotected to obtain the target product (.0.3 g).

Its infrared spectrum and NMR spectrum were consistent with those of Example 17.

EXAMPLE 35 p-Methoxybenzyl 7β-[3,4-methylenedioxybenzylidene)amino-3-[(E)-3-[((R)-1-carbamoyl-2-hydroxyethyl)dimethylammonio]-1-propenyl]-3-cephem-4-carboxylate·iodide Acetone (10 ml) was added to the compound (3 g) of Experiment 34, followed by a dropwise addition of a solution of sodium iodide (1.71 g) in acetone (20 ml) over 45 minutes under ice cooling. The resulting mixture was stirred for 3 hours at room temperature. Ethyl acetate (50 ml) was added to the solution, followed by filtration. The filtrate was washed with a 10%. aqueous solution of sodium thiosulfate and then with saturated saline. Activated carbon and anhydrous magnesium sulfate were added. After stirring the resulting mixture, silica gel (50 g) was added. The resulting mixture was filtered. The filtrate was concentrated to 30 ml, to which a solution of (R)-2-dimethylamino-3-hydroxypropionamide (903 mg) in acetone (15 ml) was added dropwise over 30 minutes. The resulting mixture was stirred for further 2 hours. Isopropyl ether (50 ml) was added to the reaction mixture. A brown semi-solid matter thus formed was collected and then dissolved in acetone (50 ml). The solution was added to ethyl ether (1 l). A precipitate thus formed was collected by filtration, and washed with ethyl acetate and then with ethyl ether to obtain the target product (1.7 g).

Infrared spectrum (cm$^{-1}$, Nujol): 1760, 1680, 1590.

NMR spectrum (δ, DMSO-d$_6$): 3.16(3H, br), 3.20(3H, br), 3.0–4.4(7H, m), 3.77(3H, s), 5.24(2H, br), 5.40(1H, d, J=5.4Hz), 5.68(1H, d, J=5.4Hz), 6.12(2H, s), 5.9–6.5(1H, m), 6.8–7.5(8H, m), 7.86(1H, br), 8.08(1H, br), 8.50(1H, br).

EXAMPLE 36

7β-Amino-3-[(E)-3-[((R)-1-carbamoyl-2-hydroxyethyl)dimethylammonio]-1-propenyl]-3-cephem-4-carboxylate perchlorate

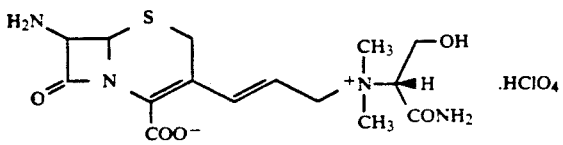

90% Formic acid (5 ml) was added to the compound (1.6 g) of Example 35, followed by an addition of 35% hydrochloric acid (1 ml) under ice cooling over 30 minutes. The resulting mixture was stirred at the same temperature for 30 minutes and then at room temperature for 1 hour. A small amount of activated carbon was added and then filtered off. The filtrate was added to acetone (800 ml), and a precipitate thus formed was collected by filtration. The precipitate was washed with acetone and ethyl ether to obtain the target product as its hydrochloride (0.71 g).

The hydrochloride (0.6 g) was dissolved in water (30 ml). After adjusting the pH of the resulting mixture to 7–8 with dilute aqueous ammonia, the mixture was filtered. The filtrate was purified by chromatography on a column packed with "SEPABEADS SP207". Relevant fractions were concentrated to 5 ml. The pH of the resulting concentrate was adjusted to 2–3 by adding 70% perchloric acid. Isopropanol (80 ml) was added. A precipitate thus formed was collected by filtration and then washed with acetone and ethyl ether to obtain the target product (0.2 g). Its infrared spectrum and NMR spectrum were consistent with those of Example 9.

EXPERIMENT 35

2-Benzothiazolylthio 2-(5-amino-1,2,4-thiadiazol-3-yl)-(Z)-2-fluoromethoxyiminoacetate

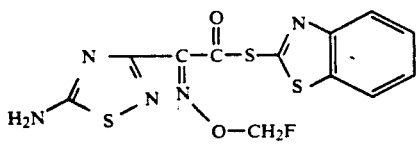

To dry dichloromethane (20 ml), were added triphenylphosphine (1.79 g) and 2,2'-benzothiazolyl disulfide (2.27 g). The resulting mixture was stirred for 30 minutes at room temperature. Under ice cooling, 2 (5-amino-1,2,4-thiadiazol-3-yl)-(Z)-2-fluoromethoxyiminoacetic acid (1 g) was added, followed by stirring for 1 hour. After concentrating the reaction mixture, it was purified by chromatography on a silica gel column to obtain the target product (230 g).

Melting point: 152–153° C. (decomposed).

Mass spectrum (m/e): 370(M$^+$ +1).

Infrared spectrum (cm$^{-1}$, Nujol): 1715, 1625, 1530.

NMR spectrum (δ, DMSO-d$_6$): 5.91(2H, d, J=54.5Hz), 7.4–7.7(2H, m), 7.9–8.3(2H, m), 8.39(2H, br).

EXAMPLE 37

7β-[2-(5-Amino-1,2,4-thiadiazol-3-yl)-(Z)-2-fluoromethoxyiminjoacetamido]-3-[(E)..3-[((R)-1-carbamoyl-2-hydroxyethyl)dimethylammonio]-1-propenyl]-3-cephem-4-carboxylate

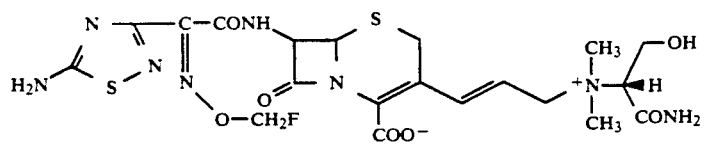

Sodium acetate trihydrate (75 mg) and 7β-amino-3-[((R)-1-carbamoyl-2-hydroxyethyl)dimethylammonio]-1-propenyl]-3-cephem-4-carboxylate (50 mg) of Example 30 were dissolved in a mixed solvent of water (0.5 ml) and methanol (3 ml). The resulting mixture was added further with 2-benzothiazolylthio 2-(5-amino-1,2,4-thiadiazol-3-yl)-(Z)-2-fluoromethoxyiminoacetate (50 mg) of Experiment 35. The resulting mixture is stirred for 3 hours at room temperature. Methanol was distilled off and the residue was purified by reversed phase chromatography on a silica gel column to obtain the target product (25 mg).

Its infrared spectrum and NMR spectrum were consistent with those of Example 10.

EXAMPLE 38

7β-[2-(5-Tritylamino-1,2,4-thiadiazol-3-yl)(Z)-2-fluoromethoxyiminoacetamido]-3-[(E)-3-[((R)-1-carbamoyl-2-hydroxyethyl)dimethylammonio]-1-propenyl]-3-cephem-4-carboxylate

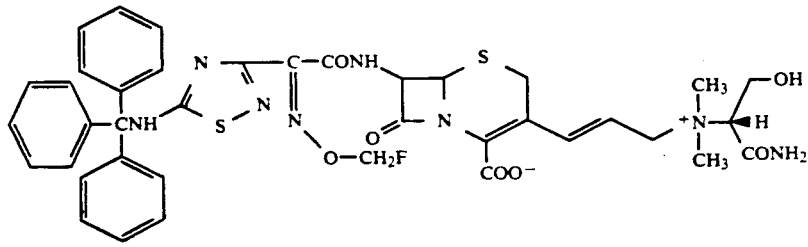

Phosphorus oxychloride (0.21 ml) was added under ice cooling to a liquid mixture of dry N,N-dimethylformamide (0.17 ml) and dry tetrahydrofuran (2 ml). After stirring the resulting mixture for 1 hour, the compound (568 mg) of Experiment 2 was added, followed by stirring for additional 1 hour. The compound (500 mg) of Example 30 and sodium acetate trihydrate (750 mg) were dissolved in a mixed solvent of water (5 ml) and methanol (30 ml), to which the above reaction mixture was added dropwise under ice cooling. The resulting The compound (500 mg) of Example 38 was suspended in anisole (3 ml), followed by an addition of trifluoroacetic acid (3.5 ml) under ice cooling. The resulting mixture was stirred for 1 hour at the same temperature, followed by a further addition of trifluoroacetic acid (1.5 ml). The resulting mixture was stirred for 1 hour. Ethyl ether was added, and a precipitate thus formed was collected by filtration to obtain the target product (350 mg). Its infrared spectrum and NMR spectrum were consistent with those of Example 10.

EXAMPLE 40

7β-[2-(5-Tritylamino-1,2,4-thiadiazol-3-yl)-(Z)-2-fluoromethoxyiminoacetamido]-3-[(E)-3-(carbamoylmethylethylmethylammonio)-1-propenyl]-3-cephem-4-carboxylate

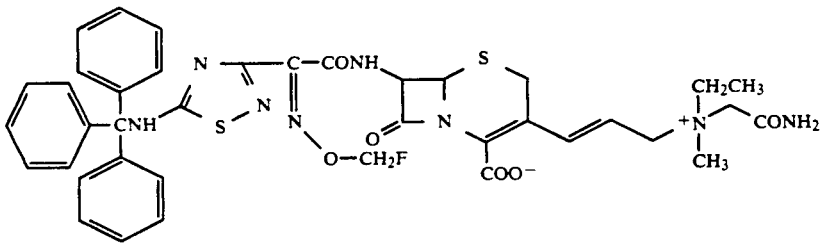

mixture was stirred for 2 hours at the same temperature. Methanol was distilled off, and a precipitate thus formed was collected by filtration and washed with water. The precipitate was added with ethyl ether which contained 5% of ethanol, followed by grinding and washing to obtain the target product (710 mg).

Infrared spectrum (cm⁻¹, Nujol) 1775, 1685.

NMR spectrum (δ, DMSO-d₆): 3.08(3H, s), 3.14(3H, s), 3.5–4.4(7H, m), 5.07(1H, d, J=5.0Hz), 5.66(1H, dd, J=5.5Hz, 8.0Hz), 5.74(2H, d, J=54.5Hz), 5.75–6.2(1H, m), 7.05(1H, d, J=15.8Hz), 7.26(15H, s), 7.72(1H, br), 8.46(1H, br), 9.66(1H, d, J=8.0Hz), 10.04(1H, s).

In a similar manner as in Example 38, the compound (1.14 g) of Experiment 2 and the compound (1 g) of Example 27 were reacted to obtain the target product (1.2 g).

Infrared spectrum (cm⁻¹, Nujol) 1770, 1675.

NMR spectrum (δ, DMSO-d₆): 1.24(3H, br), 3.06(3H, br), 3.2–4.3(8H, m), 5.05(1H, d, J=5.0Hz), 5.64(1H, dd, J=5.0Hz, 8.0Hz), 5.72(2H, d, J=54Hz), 5.7–6.2(1H, m), 7.28(15H, s), 7.60(1H, br), 8.36(1H, br), 9.69(1H, d, J=8.0Hz), 10.24(1H, s).

EXAMPLE 39

7β[2-(5-Amino-1,2,4-thiadiazol-3-yl)-(Z)-2-fluoromethoxyiminoacetamido]-3-[(E)-3-[((R)-1-carbamoyl-2-hydroxyethyl)dimethylammonio]-1-propenyl]-3-cephem-4-carboxylate

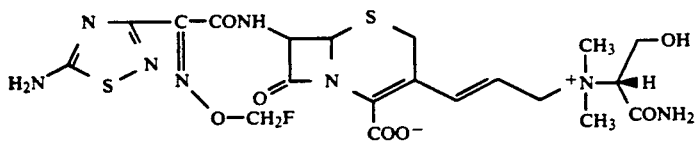

EXAMPLE 41

7β-[2-(5-Amino-1,2,4-thiadiazol-3-yl)-(Z)-2-fluoromethoxyiminoacetamido]-3-[(E)-3-(carbamoylmethylethylmethylammonio)-1-propenyl]-3-cephem-4-carboxylate

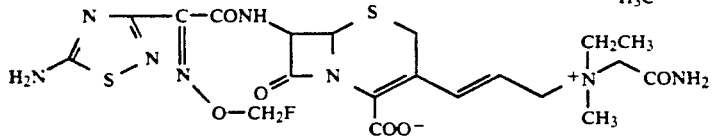

In a similar manner as in Example 39, the protecting group was removed from the compound (450 mg) of Example 40 to obtain the target product (300 mg). Its infrared spectrum and NMR spectrum were consistent with those of Example 14.

EXAMPLE 42

(R)-2-Dimethylamino-3-hydroxypropionamide

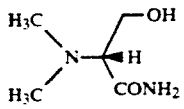

a) (R)-2-Dimethylamino-3-hydroxypropionic acid:

D-Serine (20.0 g) was dissolved in a liquid mixture of water (100 ml) and acetic acid (180 ml), followed by addition of a 37% aqueous solution of formaldehyde (35.5 ml) and platinum oxide (0.45 g). The resulting mixture was shaken overnight at room temperature in a hydrogen gas stream (3 kg/cm²) The catalyst was filtered off and the solvent was distilled off. The residue was recrystallized from acetone, thereby obtaining the target product (23.5 g) as colorless prismatic crystals.

NMR spectrum (δ, DMSO-d6): 2.68(6H, s), 3.32(1H, dd, J=5.0Hz, 6.0Hz), 3.72(1H, dd, J=6.0Hz, 12.0Hz), 3.88(1H, dd, J=5.0Hz, 12.0Hz).

b) Methyl (R)-2-dimethylamino-3-hydroxypropionate:

The compound (10 g) of the above procedure a) was dissolved in 1.5% (v/v) sulfuric acid-methanol solution (800 ml). The solution was heated for 3 days while removing moisture from refluxing methanol by a molecular sieve. The reaction mixture was ice-cooled. After a dropwise addition of concentrated (28%) aqueous ammonia (13 ml), the mixture was concentrated to 100 ml. A dilute aqueous solution of sodium bicarbonate was added, followed by extraction with chloroform. After drying the extract, the solvent was distilled off to obtain the target product (9.24 g) in a colorless oily form.

Mass spectrum (m/e): 147(M+).

Infrared spectrum (cm⁻¹, Nujol) 1735.

NMR spectrum (δ, CDCl3): 2.38(6H, s), 2.68(1H, br), 3.33(1H, t, J=7.5Hz), 3.62(1H, dd, J=7.5Hz, 11.0Hz), 3.70(3H, s), 3.80(1H, dd, J=7.5Hz, 11.0Hz).

c) (R)-2-Dimethylamino-3-hydroxypropionamide:

28% aqueous ammonia (1 ml) was added to the compound (138 mg) of the above procedure b), followed by stirring at 4° C. for 4 days. The solvent was distilled off and the residue was extracted with chloroform. The solvent was distilled off from the extract to obtain the target product (30 mg). Its mass spectrum, infrared spectrum and NMR spectrum were consistent with those of Example 2.

EXAMPLE 43

(R)-2-Dimethylamino-3-hydroxypropionamide

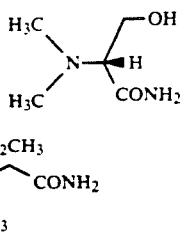

a) (R)-2-Benzylamino-3-hydroxypropionic acid:

D-Serine (5.25 g) was dissolved in a 2N aqueous solution of sodium hydroxide (25 ml) under ice cooling, followed by a dropwise addition of benzaldehyde (5.05 ml) under stirring. The resulting mixture was stirred for further 40 minutes. Sodium borohydride (0.57 g) was added and while maintaining the temperature of the resulting mixture at 15° C or lower, the mixture was stirred for 30 minutes. The same amounts of benzaldehyde and sodium borohydride were added again in the same manner, followed by stirring for 2 hours. After washing the reaction mixture twice with ethyl ether, the reaction mixture was neutralized with 1N hydrochloric acid under ice cooling. Deposited crystals were collected by filtration and then washed with water, thereby obtaining the target product (2.5 g).

Melting point 234–235° C. (decomposed).

Mass spectrum (m/e): 196(M+ +1).

b) (R)-2-Benzylmethylamino-3-hydroxypropionic acid:

The compound (2 g) of the above procedure a) was dissolved in a liquid mixture of formic acid (1.17 ml) and a 37% aqueous solution of formaldehyde (1 ml). The resulting solution was heated for 20 minutes over a boiling water bath. The solvent was distilled off and the residue was recrystallized from acetone to obtain the target product (1.5 g) as colorless prismatic crystals.

Melting point: 174–175° C. (decomposed).

Mass spectrum (m/e): 210(M+ +1).

Infrared spectrum (cm⁻¹, Nujol) 1610.

NMR spectrum (δ, DMSO-d6): 2.29(3H, s), 3.31(1H, t, J=6.7Hz), 3.62(1H, dd, J=6.7Hz, 11.0Hz), 3.77(2H, s), 3.80(1H, dd, J=6.7Hz, 11.0Hz), 7.30(5H, br).

c) (R)-2-Benzylmethylamino-3-hydroxypropionamide:

The compound (500 mg) of the above procedure b) was suspended in tetrahydrofuran (7.5 ml). Under cooling at −20° C., were added dropwise N-methylmorpholine (0.41 ml) and then isobutyl chloroformate (0.49 ml). The resulting mixture was stirred for 15 minutes at the same temperature. The solution was then cooled to −50° C., and ammonia gas was blown into the solution until no temperature rise was observed. The solution was then added with water, followed by extraction with ethyl acetate. The ethyl acetate layer was extracted with 1N hydrochloric acid. After alkalinization of the water layer with concentrated aqueous ammonia, it was extracted again with ethyl acetate. After drying the extract over anhydrous magnesium sulfate, the solvent was distilled off to obtain the target product (320 mg).

Melting point: 87–88° C.

Mass spectrum (m/e): 209(M+ +1).

Infrared spectrum (cm$^{-1}$, Nujol) 1665.

NMR spectrum (δ, DMSO-d$_6$): 2.16(3H, s), 3.12(1H, t, J=6.5Hz), 3.4–3.8(4H, m), 4.54(1H, t, J=5.5Hz), 6.9–7.35(7H, m).

d) Benzyl((R)-1-carbamoyl-2-hydroxyethyl)dimethylammonium·bromide:

The compound (450 mg) of the above procedure c) was dissolved in acetone (2 ml), followed by an addition of methyl bromide (3.2 ml). The resulting mixture was allowed to stand overnight at room temperature. The reaction mixture was added dropwise to petroleum ether under stirring, thereby obtaining the target product (300 mg).

Mass spectrum (m/e): 223(M$^+$-Br)

Infrared spectrum (cm$^{-1}$, Nujol): 1670.

NMR spectrum (δ, DMSO-d$_6$): 3.10(3H, s), 3.18(3H, s), 3.9–4.4(3H, m), 4.69(1H, d, J=12.5Hz), 4.93(1H, d, J=12.5Hz), 5.74(1H, br), 7.81(1H, br), 8.14(1H, br).

e) (R)-2-Dimethylamino-3-hydroxypropionamide:

The compound (700 mg) of the above procedure d) was dissolved in methanol (7 ml), followed by an addition of 10% Pd-C catalyst (70 mg). The resulting mixture was shaken at room temperature for 2 hours in a hydrogen gas stream (3 kg/cm$^2$). The catalyst was filtered off. A 1N aqueous solution of sodium hydroxide (2.2 ml) was added to the filtrate under ice cooling, followed by extraction with chloroform (50 ml). The solvent was distilled off from the extract to obtain the target product (300 mg). Its mass spectrum, infrared spectrum and NMR spectrum were consistent with those of Example 2.

EXAMPLE 44

(R)-2-Dimethylamino-3-hydroxypropionamide

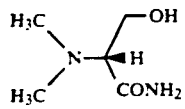

D-Serine amide hydrochloride (50 g) was dissolved in a liquid mixture of water (250 ml) and acetic acid (125 ml). At room temperature, a 37% aqueous solution of formaldehyde (63.5 g) was added, followed by stirring. The resulting mixture was then heated to 50° C., followed by addition of zinc powder (53.5 g) and a 10% aqueous solution of cobalt sulfate (5.4 ml). The resulting mixture was stirred for one and a half hours at the same temperature. Zinc powder was filtered off by means of "Celite" (trade mark for diatomaceous earth; product of Manville Corp.). Oxalic acid dihydrate (103.2 g) was added to the filtrate, followed by stirring for 5 minutes An insoluble matter was filtered off and the filtrate was concentrated under reduced pressure. The residue was purified by chromatography on an alumina column. Fractions containing the target product were concentrated to obtain an oily substance of a pale yellow color (30 g). It was recrystallized from ethanol-isopropyl ether to obtain the target product (21.8 g).

Melting point: 57–61° C.

Specific rotation [α]$_D$: +20.3 (C=1.009, ethanol).

Its mass spectrum, infrared spectrum and NMR spectrum were consistent with those of Example 2.

We claim:

1. A compound represented by the following formula:

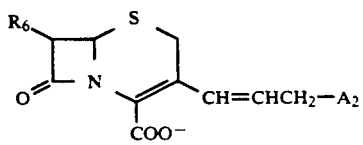

wherein R$_6$ means amino, 2-phenylacetamido, formamido, (3-nitrobenzylidene)-amino, or (3,4-methylenedioxybenzylidene) amino and A$_2$ denotes a group represented by the following formula:

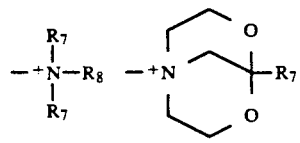

all R$_7$ being either the same or different and meaning individually a lower alkyl group and R$_8$ denoting a lower alkyl group substituted by a hydroxyl group and/or a carbamoyl group, a compound obtained by blocking —COO$^-$ of the first-mentioned compound with a protecting group, or a salt thereof.

2. 7β-Amino-3-[(E)-3-[((R)-1-carbamoyl-2-hydroxyethyl)dimethylammonio]-1-propenyl]-3-cephem-4-carboxylate or perchlorate thereof.

3. 7β-Amino-3-[(E)-3(carbamoylmethylethylmethylammonio)-1-propenyl]-3-cephem-4-carboxylate or paratoluenesulfonate thereof.

* * * * *